(12) United States Patent
LaVon et al.

(10) Patent No.: US 7,320,684 B2
(45) Date of Patent: Jan. 22, 2008

(54) DISPOSABLE ABSORBENT ARTICLE HAVING DEPLOYABLE BELT STRIPS

(75) Inventors: Gary Dean LaVon, Liberty Township, OH (US); Kenneth Michael Hamall, West Chester, OH (US); Theodora Beck, Colerain Township, OH (US); Michael Patrick Hayden, Mason, OH (US); Susan Joy Ludwig, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/232,193

(22) Filed: Sep. 21, 2005

(65) Prior Publication Data

US 2007/0066954 A1    Mar. 22, 2007

(51) Int. Cl.
*A61F 13/15* (2006.01)
(52) U.S. Cl. ................................. 604/392; 604/396
(58) Field of Classification Search ........... 604/385.01, 604/386–387, 390–396
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |

(Continued)

FOREIGN PATENT DOCUMENTS

EP    0 206 208 A1    12/1986

(Continued)

OTHER PUBLICATIONS

U.S. Appl. No. 10/880,128, filed Jun. 29, 2004, LaVon.

(Continued)

*Primary Examiner*—Michele Kidwell
(74) *Attorney, Agent, or Firm*—Michael P. Hayden; Thibault Fayette; Matthew P. Fitzpatrick

(57) ABSTRACT

A disposable absorbent article having laterally opposing interiorly attached barrier cuff strips and at least one deployable belt strip. Each barrier cuff strip is attached to an interior surface of an absorbent assembly and has a longitudinally extending elastic gathering member attached adjacent to its proximal edge. The belt strip has a fixed end portion and opposing first and second edges connecting the fixed end portion and an opposing free end portion. The belt strip is attached in the fixed end portion and is deployed by being folded laterally outward such that the first edge extends laterally outward from one end point of a diagonal fold line and the second edge extends laterally outward from the opposing end point of the diagonal fold line. The belt strip may be tied to another belt strip or may be fastened to the waist region of the article or to another belt strip.

20 Claims, 39 Drawing Sheets

U.S. PATENT DOCUMENTS

| | | |
|---|---|---|
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,578,155 A | 5/1971 | Small et al. |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,578,072 A * | 3/1986 | Lancaster ............... 604/385.24 |
| 4,585,450 A | 4/1986 | Rosch et al. |
| 4,589,878 A | 5/1986 | Mitrani |
| 4,601,717 A | 7/1986 | Blevins |
| 4,610,678 A | 9/1986 | Weisman et al. |
| 4,636,207 A | 1/1987 | Buell |
| 4,670,011 A | 6/1987 | Mesek |
| 4,670,012 A * | 6/1987 | Johnson ...................... 604/390 |
| 4,680,030 A | 7/1987 | Coates et al. |
| 4,681,581 A | 7/1987 | Coates |
| 4,690,680 A | 9/1987 | Higgins |
| 4,695,278 A | 9/1987 | Lawson |
| 4,704,115 A | 11/1987 | Buell |
| 4,704,116 A | 11/1987 | Enloe |
| 4,731,066 A | 3/1988 | Korpman |
| 4,747,846 A | 5/1988 | Boland et al. |
| 4,795,454 A | 1/1989 | Dragoo |
| 4,802,884 A | 2/1989 | Fröidh et al. |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A | 7/1989 | Enloe et al. |
| 4,861,652 A | 8/1989 | Lippert et al. |
| 4,888,231 A | 12/1989 | Angstadt |
| 4,892,528 A | 1/1990 | Suzuki et al. |
| 4,892,536 A | 1/1990 | DesMarais et al. |
| 4,904,251 A | 2/1990 | Igaue et al. |
| 4,909,802 A | 3/1990 | Ahr et al. |
| 4,909,803 A | 3/1990 | Aziz et al. |
| 4,940,463 A | 7/1990 | Leathers et al. |
| 4,940,464 A | 7/1990 | Van Gompel et al. |
| 4,950,264 A | 8/1990 | Osborn |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,037,416 A | 8/1991 | Allen et al. |
| 5,071,414 A | 12/1991 | Elliott |
| 5,085,654 A | 2/1992 | Buell |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A | 9/1993 | Minetola et al. |
| 5,246,432 A | 9/1993 | Suzuki et al. |
| 5,246,433 A | 9/1993 | Hasse et al. |
| 5,260,345 A | 11/1993 | Desmarais et al. |
| 5,269,775 A | 12/1993 | Freeland et al. |
| 5,304,162 A * | 4/1994 | Kuen ......................... 604/391 |
| 5,312,386 A | 5/1994 | Correa et al. |
| 5,358,500 A | 10/1994 | LaVon et al. |
| 5,366,782 A | 11/1994 | Curro et al. |
| 5,387,209 A | 2/1995 | Yamamoto et al. |
| 5,397,316 A | 3/1995 | LaVon et al. |
| H1440 H | 5/1995 | New et al. |
| 5,476,458 A | 12/1995 | Glaug et al. |
| 5,518,801 A | 5/1996 | Chappell et al. |
| 5,531,730 A | 7/1996 | Dreier |
| 5,549,593 A | 8/1996 | Ygge et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,584,829 A | 12/1996 | Lavash et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,622,589 A | 4/1997 | Johnson et al. |
| 5,624,424 A | 4/1997 | Saisaka et al. |
| 5,625,222 A | 4/1997 | Yoneda et al. |
| 5,626,571 A | 5/1997 | Young et al. |
| 5,635,191 A | 6/1997 | Roe et al. |
| 5,643,588 A | 7/1997 | Roe et al. |

| | | | |
|---|---|---|---|
| H1674 H | 8/1997 | Ames et al. | |
| 5,662,638 A | 9/1997 | Johnson et al. | |
| 5,674,215 A | 10/1997 | Ronnberg | |
| 5,691,035 A | 11/1997 | Chappell et al. | |
| 5,691,036 A | 11/1997 | Lin et al. | |
| 5,723,087 A | 3/1998 | Chappell et al. | |
| 5,749,866 A | 5/1998 | Roe et al. | |
| 5,752,947 A | 5/1998 | Awolin | |
| 5,772,825 A | 6/1998 | Schmitz | |
| 5,779,831 A | 7/1998 | Schmitz | |
| 5,797,894 A | 8/1998 | Cadieux et al. | |
| 5,810,800 A | 9/1998 | Hunter et al. | |
| 5,814,035 A | 9/1998 | Gryskiewicz et al. | |
| 5,846,232 A | 12/1998 | Serbiak et al. | |
| 5,851,204 A | 12/1998 | Mizutani | |
| 5,865,823 A | 2/1999 | Curro | |
| 5,873,868 A | 2/1999 | Nakahata | |
| 5,876,391 A | 3/1999 | Roe et al. | |
| 5,891,544 A | 4/1999 | Chappell et al. | |
| 5,897,545 A | 4/1999 | Kline et al. | |
| 5,904,673 A | 5/1999 | Roe et al. | |
| 5,951,536 A | 9/1999 | Osborn, III et al. | |
| 5,957,908 A | 9/1999 | Kline et al. | |
| 5,968,029 A | 10/1999 | Chappell et al. | |
| 6,004,306 A | 12/1999 | Robles et al. | |
| 6,022,430 A | 2/2000 | Blenke et al. | |
| 6,022,431 A | 2/2000 | Blenke et al. | |
| 6,042,673 A | 3/2000 | Johnson et al. | |
| 6,102,892 A | 8/2000 | Putzer et al. | |
| 6,107,537 A | 8/2000 | Elder et al. | |
| 6,110,157 A | 8/2000 | Schmidt | |
| 6,117,121 A | 9/2000 | Faulks et al. | |
| 6,120,486 A | 9/2000 | Toyoda et al. | |
| 6,120,487 A | 9/2000 | Ashton | |
| 6,120,489 A | 9/2000 | Johnson et al. | |
| 6,120,866 A | 9/2000 | Arakawa et al. | |
| 6,129,720 A | 10/2000 | Blenke et al. | |
| 6,156,424 A | 12/2000 | Taylor | |
| 6,165,160 A | 12/2000 | Suzuki et al. | |
| 6,174,302 B1 | 1/2001 | Kumasaka | |
| 6,186,996 B1 | 2/2001 | Martin | |
| 6,210,390 B1 | 4/2001 | Karlsson | |
| 6,238,380 B1 | 5/2001 | Sasaki | |
| 6,241,716 B1 | 6/2001 | Rönnberg | |
| 6,322,552 B1 | 11/2001 | Blenke et al. | |
| 6,325,787 B1 | 12/2001 | Roe et al. | |
| 6,334,858 B1 | 1/2002 | Rönnberg et al. | |
| 6,350,332 B1 | 2/2002 | Thomas et al. | |
| 6,402,729 B1 | 6/2002 | Boberg et al. | |
| 6,402,731 B1 | 6/2002 | Suprise et al. | |
| 6,410,820 B1 | 6/2002 | McFall et al. | |
| 6,413,249 B1 | 7/2002 | Turi et al. | |
| 6,419,667 B1 | 7/2002 | Avalon et al. | |
| 6,432,098 B1 | 8/2002 | Kline et al. | |
| 6,432,099 B2 | 8/2002 | Rönnberg | |
| 6,443,933 B1 | 9/2002 | Suzuki et al. | |
| 6,461,342 B2 | 10/2002 | Tanji et al. | |
| 6,475,201 B2 | 11/2002 | Saito et al. | |
| 6,494,872 B1 | 12/2002 | Suzuki et al. | |
| 6,494,873 B2 | 12/2002 | Karlsson et al. | |
| 6,520,947 B1 | 2/2003 | Tilly et al. | |
| 6,524,294 B1 | 2/2003 | Hilston et al. | |
| 6,579,275 B1 * | 6/2003 | Pozniak et al. | 604/390 |
| 6,585,713 B1 | 7/2003 | LeMahieu et al. | |
| 6,605,070 B2 | 8/2003 | Ludwig et al. | |
| 6,648,869 B1 | 11/2003 | Gillies et al. | |
| 6,648,870 B2 | 11/2003 | Itoh et al. | |
| 6,648,871 B2 | 11/2003 | Kusibojoska et al. | |
| 6,682,515 B1 | 1/2004 | Mizutani et al. | |
| 6,689,115 B1 | 2/2004 | Popp et al. | |
| 6,726,792 B1 | 4/2004 | Johnson et al. | |
| 6,880,211 B2 | 4/2005 | Jackson et al. | |
| 6,923,797 B2 | 8/2005 | Shinohara et al. | |
| 6,962,578 B1 | 11/2005 | LaVon | |
| 6,972,010 B2 | 12/2005 | Pesce et al. | |
| 7,014,632 B2 | 3/2006 | Takino et al. | |
| 7,037,299 B2 | 5/2006 | Turi et al. | |
| 7,048,726 B2 | 5/2006 | Kusagawa et al. | |
| 2002/0045881 A1 * | 4/2002 | Kusibojoska et al. | 604/392 |
| 2002/0087139 A1 | 7/2002 | Popp et al. | |
| 2002/0173767 A1 | 11/2002 | Popp et al. | |
| 2003/0088223 A1 | 5/2003 | Vogt et al. | |
| 2003/0144644 A1 | 7/2003 | Murai et al. | |
| 2003/0148694 A1 | 8/2003 | Ghiam | |
| 2003/0233082 A1 | 12/2003 | Kline et al. | |
| 2004/0022998 A1 | 2/2004 | Miyamoto et al. | |
| 2004/0082928 A1 | 4/2004 | Pesce et al. | |
| 2004/0122411 A1 | 6/2004 | Hancock-Cooke | |
| 2004/0147890 A1 | 7/2004 | Nakahata et al. | |
| 2004/0162536 A1 | 8/2004 | Becker et al. | |
| 2004/0167486 A1 | 8/2004 | Busam et al. | |
| 2004/0225271 A1 * | 11/2004 | Datta et al. | 604/385.11 |
| 2004/0236299 A1 | 11/2004 | Tsang et al. | |
| 2004/0249355 A1 | 12/2004 | Tanio et al. | |
| 2005/0004543 A1 | 1/2005 | Schroer et al. | |
| 2005/0004548 A1 | 1/2005 | Otsubo et al. | |
| 2005/0038401 A1 | 2/2005 | Suzuki et al. | |
| 2005/0085784 A1 | 4/2005 | LeMinh et al. | |
| 2005/0143709 A1 * | 6/2005 | Lindstrom | 604/391 |
| 2005/0171499 A1 | 8/2005 | Nigam et al. | |
| 2005/0203475 A1 | 9/2005 | LaVon et al. | |
| 2005/0288645 A1 | 12/2005 | LaVon | |
| 2005/0288646 A1 | 12/2005 | LaVon | |
| 2006/0264860 A1 | 11/2006 | Beck | |
| 2007/0049897 A1 * | 3/2007 | LaVon et al. | 604/392 |

FOREIGN PATENT DOCUMENTS

| | | |
|---|---|---|
| EP | 0 403 832 B1 | 12/1990 |
| EP | 0 761 194 A2 | 3/1997 |
| EP | 0 893 115 A2 | 1/1999 |
| EP | 0 916 327 B1 | 5/1999 |
| EP | 0 951 890 A2 | 10/1999 |
| EP | 0 793 469 B9 | 6/2002 |
| EP | 1 224 922 A2 | 7/2002 |
| EP | 1 447 066 A1 | 8/2004 |
| EP | 1 447 067 A1 | 8/2004 |
| ES | 2 213 491 A1 | 8/2004 |
| FR | 2 566 631 A1 | 1/1986 |
| FR | 2 612 770 A1 | 9/1988 |
| FR | 2 810 234 A1 | 12/2001 |
| GB | 1 307 441 | 2/1973 |
| GB | 1 513 055 | 6/1978 |
| GB | 2 101 468 A | 1/1983 |
| GB | 2 262 873 A | 7/1993 |
| JP | 04 122256 A | 4/1992 |
| JP | 11318980 | 11/1999 |
| WO | WO 95/29657 A1 | 11/1995 |
| WO | WO 98/16179 A1 | 4/1998 |
| WO | WO 99/13813 A1 | 3/1999 |
| WO | WO 03/009794 A3 | 2/2003 |
| WO | WO 2004/105664 | 12/2004 |
| WO | WO 2005/087164 A1 | 9/2005 |
| WO | WO 2007/000315 A1 | 1/2007 |

OTHER PUBLICATIONS

U.S. Appl. No. 11/158,563, filed Jun. 22, 2005, LaVon et al.
U.S. Appl. No. 11/231,511, filed Sep. 21, 2005, LaVon et al.
U.S. Appl. No. 11/231,512, filed Sep. 21, 2005, LaVon et al.
U.S. Appl. No. 11/231,500, filed Sep. 21, 2005, LaVon et al.
U.S. Appl. No. 11/286,612, filed Nov. 23, 2005, LaVon.

* cited by examiner

DISPOSABLE ABSORBENT ARTICLE HAVING DEPLOYABLE BELT STRIPS

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. Among these are often complex waist closure components for application onto the body of a wearer. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a disposable absorbent article having simple and cost-effective waist closure means.

SUMMARY OF THE INVENTION

The present invention is a disposable absorbent article having laterally opposing interiorly attached barrier cuff strips and at least one deployable belt strip. Each barrier cuff strip is attached to an interior surface of an absorbent assembly and has a longitudinally extending elastic gathering member attached adjacent to its proximal edge. The belt strip has a fixed end portion and opposing first and second edges connecting the fixed end portion and an opposing free end portion. The belt strip is attached in the fixed end portion and is deployed by being folded laterally outward such that the first edge extends laterally outward from one end point of a diagonal fold line and the second edge extends laterally outward from the opposing end point of the diagonal fold line. The belt strip may be tied to another belt strip or may be fastened to the waist region of the article or to another belt strip.

BRIEF DESCRIPTION OF THE DRAWINGS

In the accompanying drawing figures, like reference numerals identify structurally corresponding elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In the drawing figures and in the written description, lowercase letters appended to reference numerals indicate generally symmetric elements, e.g., left and right symmetric elements may be respectively identified by the reference numerals 1a and 1b. A reference numeral without an appended lowercase letter identifies all of the elements to which that particular reference numeral applies, e.g., the same elements as a group may be designated 1.

DETAILED DESCRIPTION OF THE INVENTION

Figure 1:
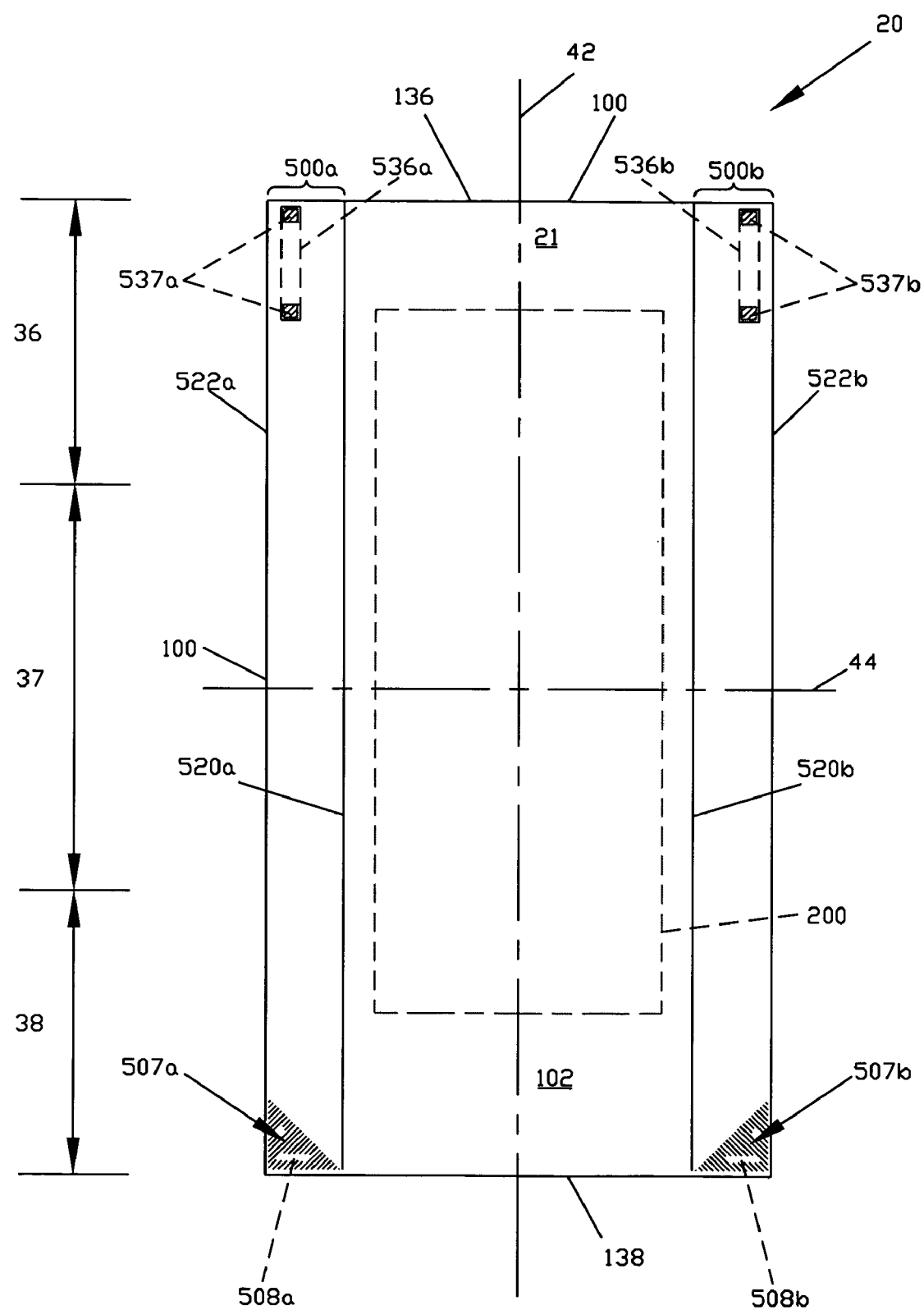
FIG. 1 is a plan view of an exemplary disposable absorbent article in the form of a disposable diaper 20 in which the interior portion of the diaper is shown facing the viewer.
Figure 2:
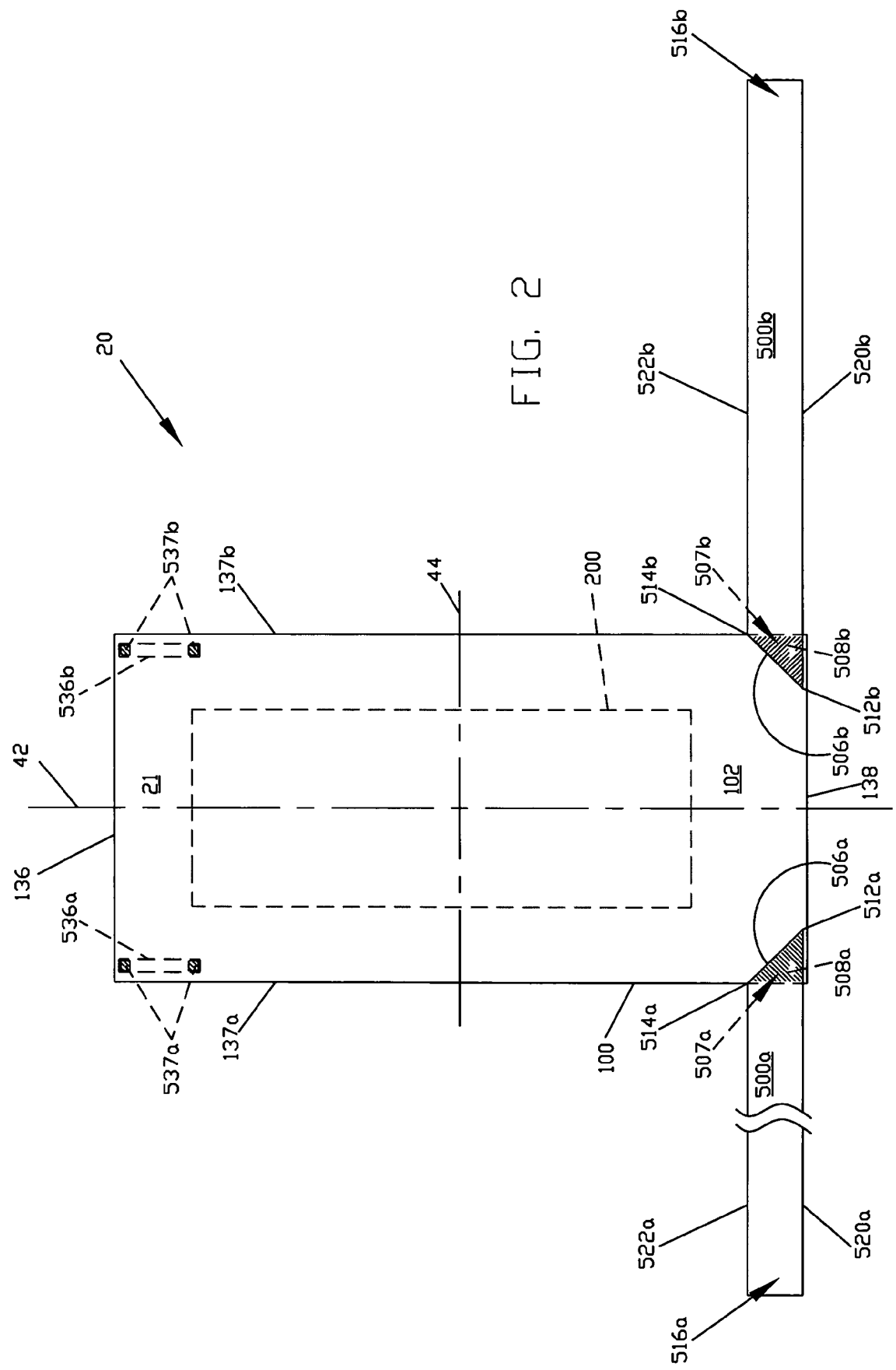
FIG. 2 is another interior plan view of the diaper 20 of FIG. 1 in which the belt strips 500 have been deployed by being folded laterally outward.
Figure 3:
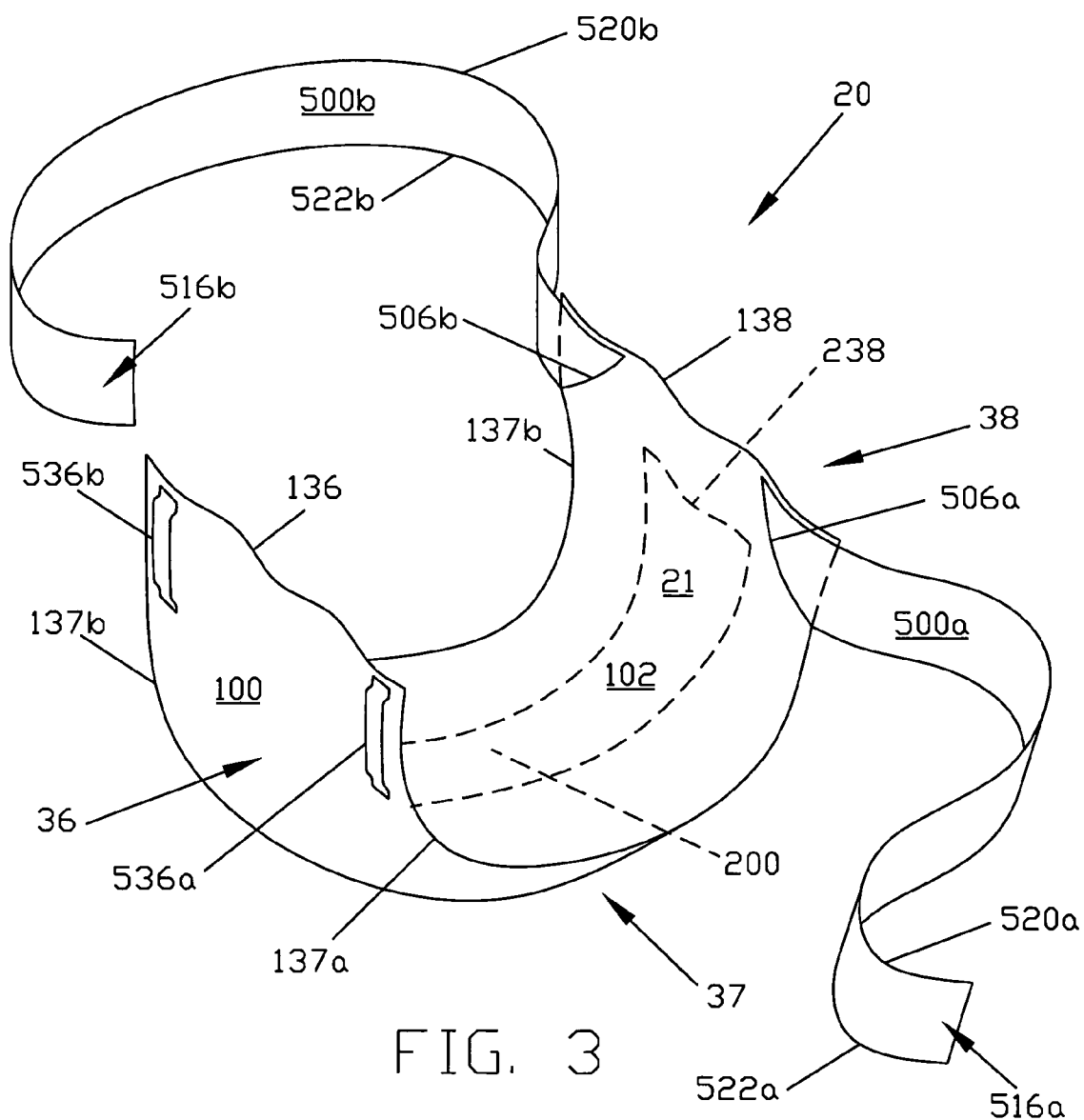
FIG. 3 is a perspective view of the diaper 20 of FIG. 2.
Figure 4:
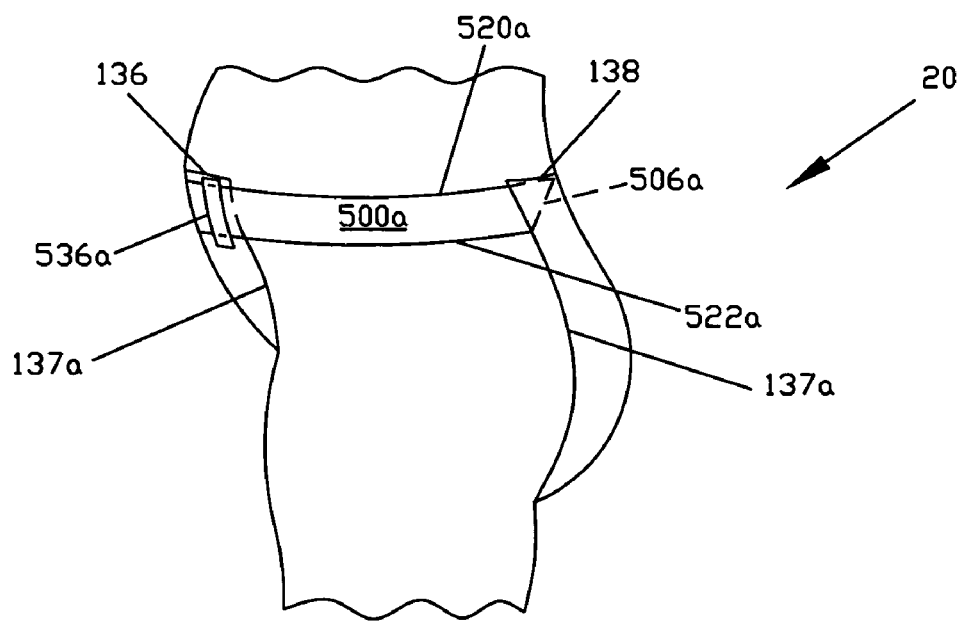
FIG. 4, FIG. 5, and FIG. 6 are respectively simplified side, front, and back elevation views of the diaper 20 of FIG. 1 being worn about the lower torso of a wearer.
Figure 5:
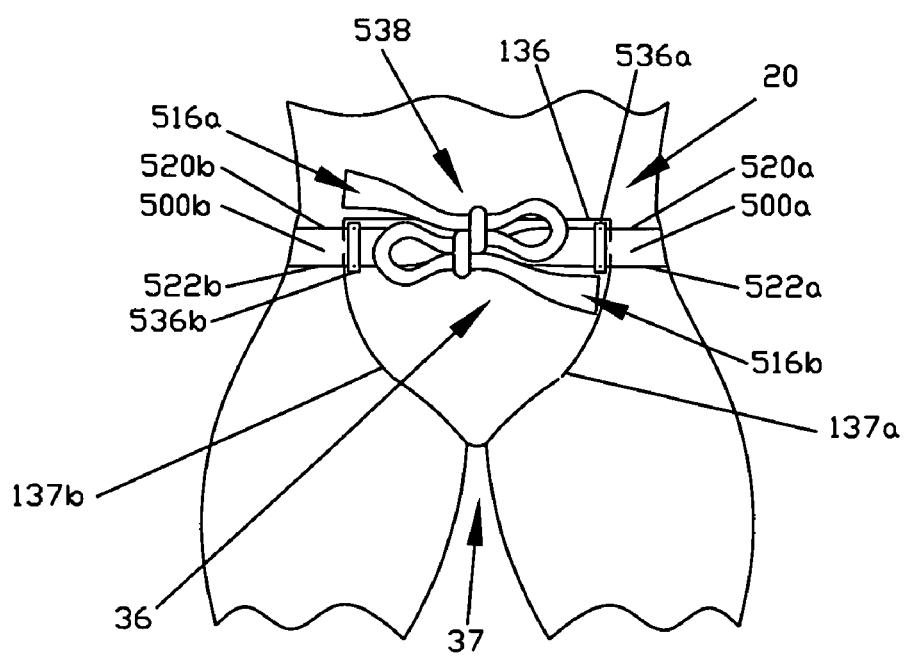
Figure 6:
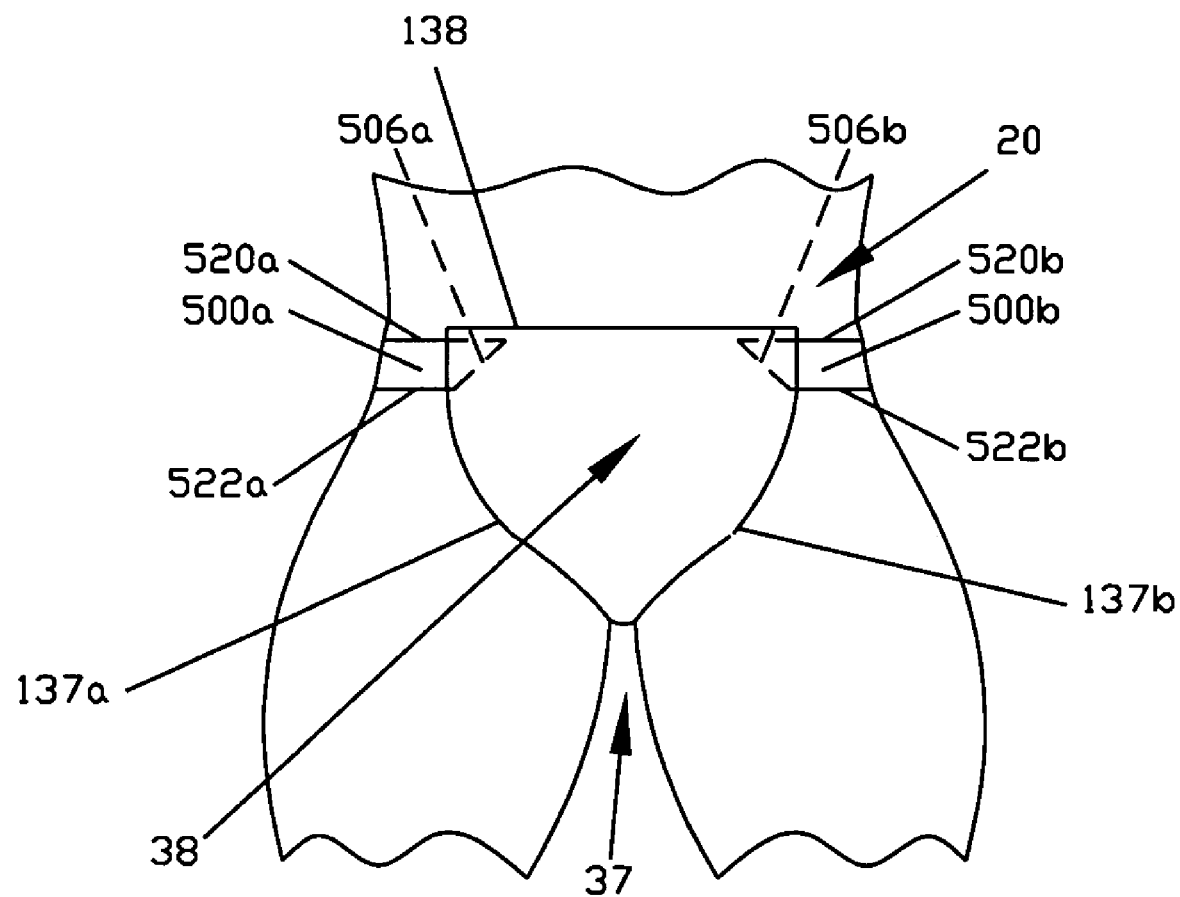

In this description, the following terms have the following meanings:

The term "absorbent article" refers to a device that absorbs and contains liquid, and more specifically, refers to a device that is placed against or in proximity to the body of a wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner. In this description, a disposable diaper is described as being representative of an exemplary disposable absorbent article.

The term "deploy" in all its forms refers to the manipulation of the disclosed belt strips from their initial configuration to a configuration in which they can be used to at least partially encircle the waist of a wearer of the article on which they are provided.

The term "longitudinal" refers to a direction running from a waist edge to an opposing waist edge of the article and generally parallel to the maximum linear dimension of the article.

The term "lateral" refers to a direction running from a side edge to an opposing side edge of the article and generally at a right angle to the longitudinal direction.

The term "diagonal" refers to an orientation of a line extending obliquely relative to the longitudinal and lateral directions, i.e., neither perpendicular nor parallel to either of the longitudinal or lateral directions.

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that, once set, sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element relatively near to or far from the center of a structure, e.g., the laterally proximal edge of a longitudinally extending element is located nearer to the longitudinal axis than the laterally distal edge of the same element is located relative to the same longitudinal axis. When used to describe relative locations with respect to the axes, synonyms include "inboard" and "outboard", respectively. The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

As can be seen in the drawing figures, one end portion of the exemplary diaper 20 is configured as a front waist region 36, the longitudinally opposing end portion is configured as a back waist region 38, and an intermediate portion is configured as a crotch region 37.

The basic structure of the diaper 20 includes a chassis 100, which has a front edge 136, a back edge 138, laterally opposing side edges 137, an interior surface 102, and an exterior surface 104. A longitudinal axis 42 extends through the midpoints of the front edge 136 and the back edge 138 and a lateral axis 44 extends through the midpoints of the side edges 137.

The basic structure of the diaper 20 also includes an absorbent assembly 200, which is attached to the chassis 100. The absorbent assembly 200 absorbs and retains liquid bodily waste materials. Suitable well-known absorbent materials for the absorbent assembly include cellulose fibers in the form of comminuted wood pulp, which is commonly known as "airfelt", layers or sheets of natural or synthetic fibrous material, superabsorbent polymer, etc. These absorbent materials may be used separately or in combination and many may be used in a discrete form, i.e., in the form of fibers, granules, particles, layers and the like. The discrete form of an absorbent material may be immobilized in pockets formed by a layer of a thermoplastic material, such as a hot melt adhesive, that intermittently contacts and adheres to a substrate, such as a covering sheet, while diverging away from the substrate at the pockets. Absorbent assemblies having such pocket structures are described in more detail in U.S. Patent Application Publications Nos. 2004/0167486 of 26 Aug. 2004 and 2004/0162536 of 19 Aug. 2004.

The basic structure of the diaper 20 also includes at least one deployable belt strip 500, as described in detail below.

When the diaper 20 is worn on the lower torso of a wearer, the front waist edge 136 and the back waist edge 138 of the chassis lie against the waist of the wearer, the side edges 137 partially or wholly encircle the legs of the wearer, the crotch region 37 is generally positioned between the legs of the wearer, and the absorbent assembly 200 extends from the front waist region 36 through the crotch region 37 to the back waist region 38.

A portion or the whole of chassis and/or the absorbent assembly and/or the belt strip may be formed of an elastically extensible material or materials. Alternatively, or in addition, a portion or the whole of chassis and/or the absorbent assembly and/or the belt strip may be made extensible to a degree greater than the inherent extensibility of the material or materials from which it is made. The additional extensibility may be desirable in order to allow the diaper 20 to conform to the body of a wearer during movement by the wearer. Additional lateral extensibility may be particularly desirable to allow the user of a diaper to extend the front waist region and/or the back waist region to encircle the waist of a wearer, i.e., to tailor the waist size and fit of a diaper to the individual wearer. Such a lateral extension of the waist region or regions may give the diaper a generally hourglass shape and may impart a tailored appearance to the diaper when it is worn. In addition, the additional extensibility may be desirable in order to minimize the cost of the diaper, because a relatively lesser amount of material is needed when the material is made extensible as described.

This additional extensibility may be provided in a variety of ways. For example, a material or materials from which the chassis and/or the absorbent assembly and/or the belt strip is/are made may be pleated by any of many known methods. Alternatively, all or a portion of the chassis and/or the absorbent assembly and/or the belt strip may be made of a formed web material or a formed laminate of web materials like those described in U.S. Pat. No. 5,518,801 issued on 21 May 1996 in the name of Chappell et al. In addition, different portions of the chassis and/or the absorbent assembly and/or the belt strip may be formed to have different ranges of extensibility and/or to be extensible to a greater or lesser degree when subjected to a given level of opposing tensile forces, i.e., to be relatively more easily or less easily extensible. Such differential extensibility may be desirable so that, for example, one or both of the waist regions may be laterally extended relatively farther or relatively more easily than the crotch region.

Unless explicitly excluded in its description or precluded by a structural characteristic unique to the particular disposition of the belt strip 500 or to the particular embodiment shown, the following description of alternatives applies to every configuration of the belt strip 500.

In FIG. 1 through FIG. 9, the belt strips 500 are shown disposed interiorly. Alternatively the belt strips 500 may be disposed exteriorly, as shown in FIG. 10 through FIG. 35.

Figure 10:
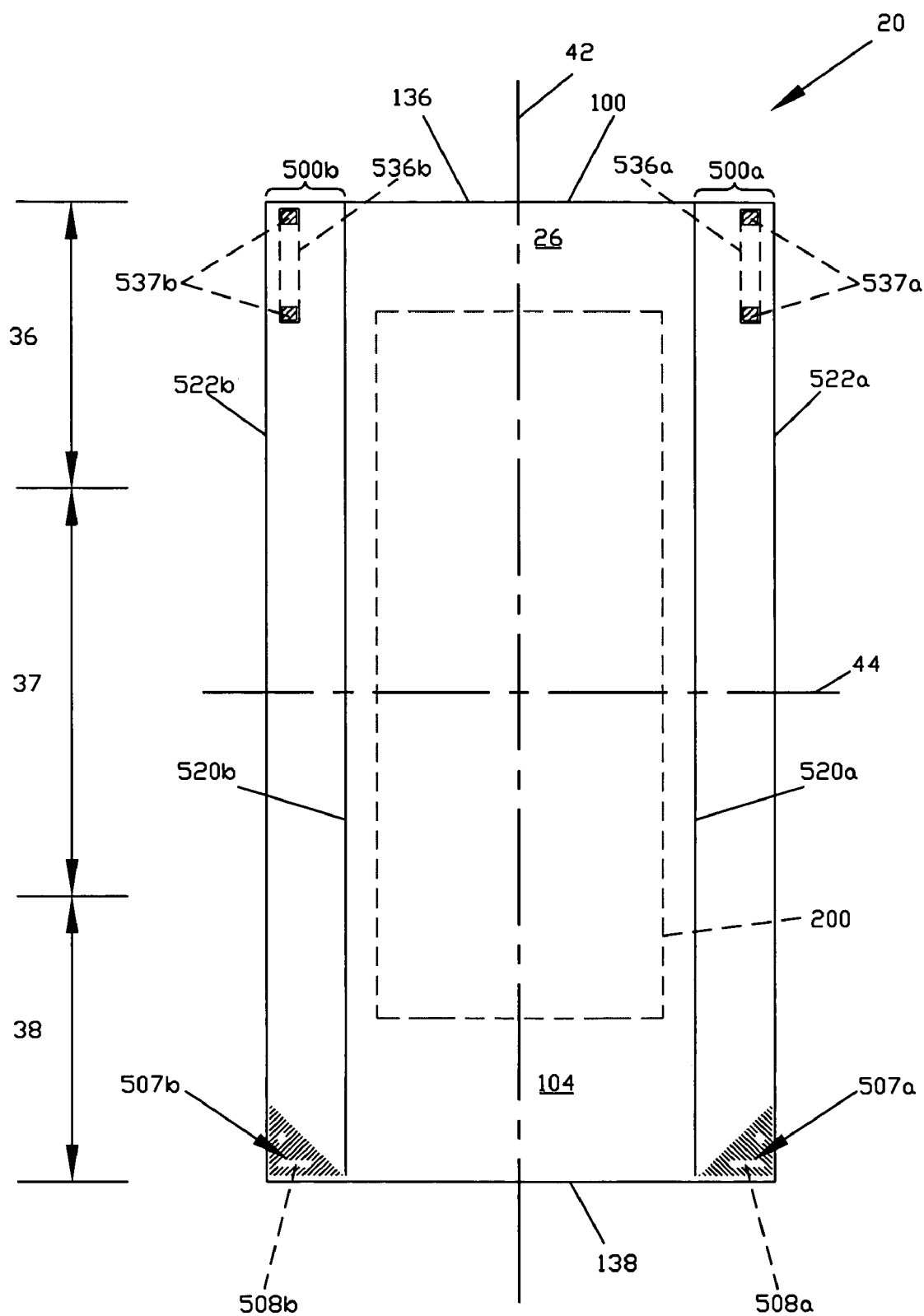
FIG. 10 is an exterior plan view of another exemplary disposable diaper 20.
Figure 11:
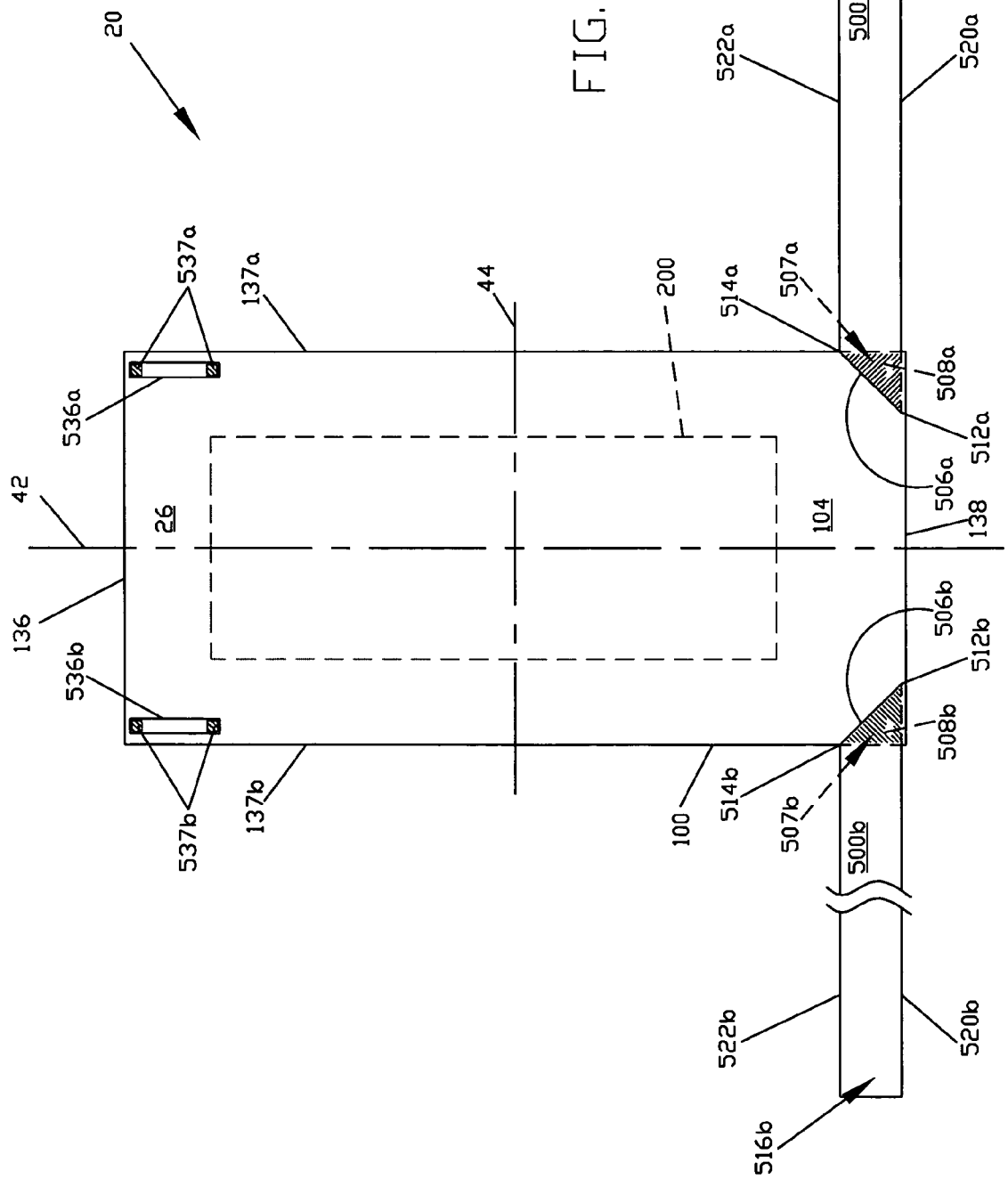
FIG. 11 is another exterior plan view of the diaper 20 of FIG. 10 in which the belt strips 500 have been deployed by being folded laterally outward.
Figure 12:
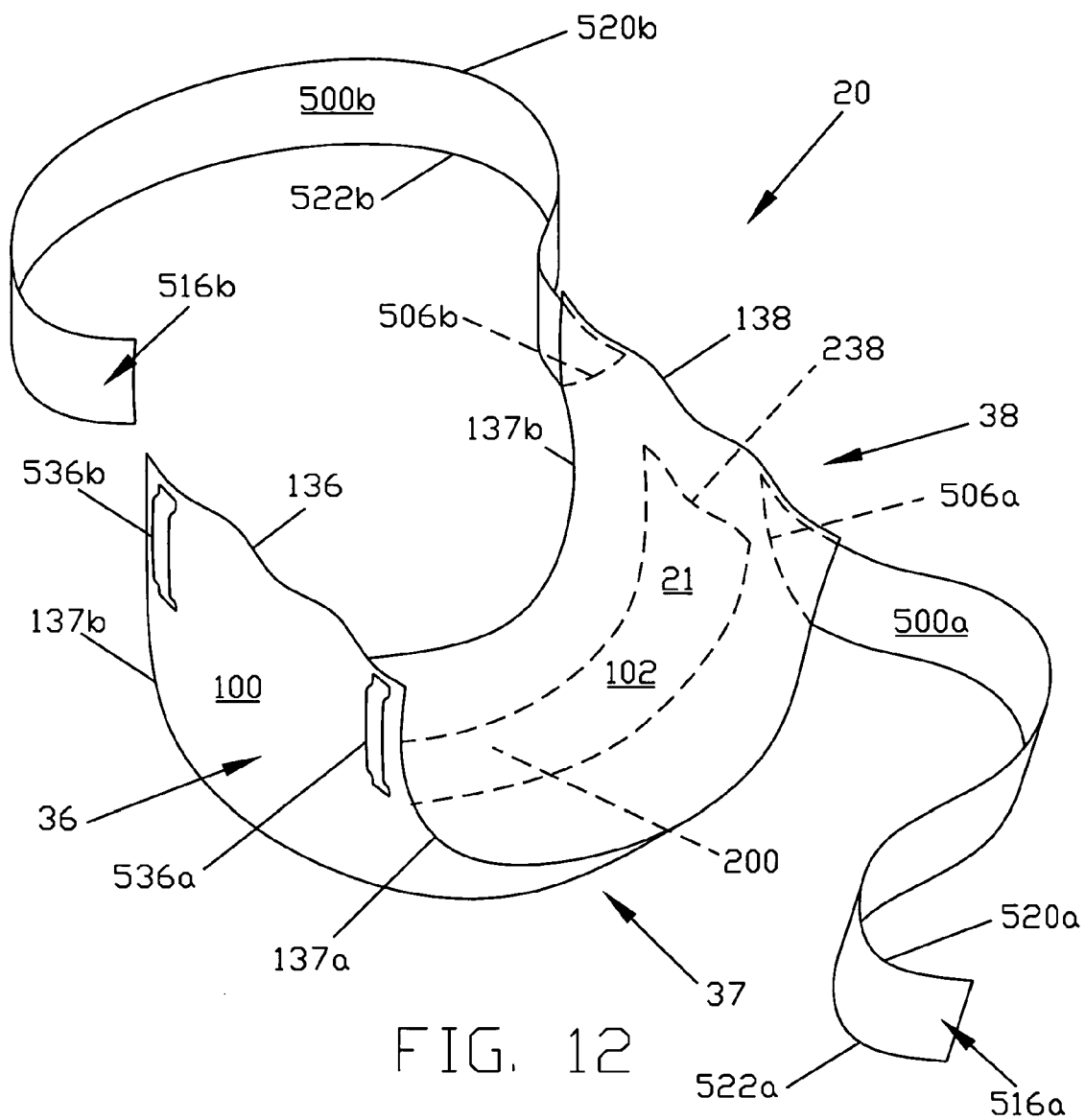
FIG. 12 is a perspective view of the diaper 20 of FIG. 11.
Figure 13:
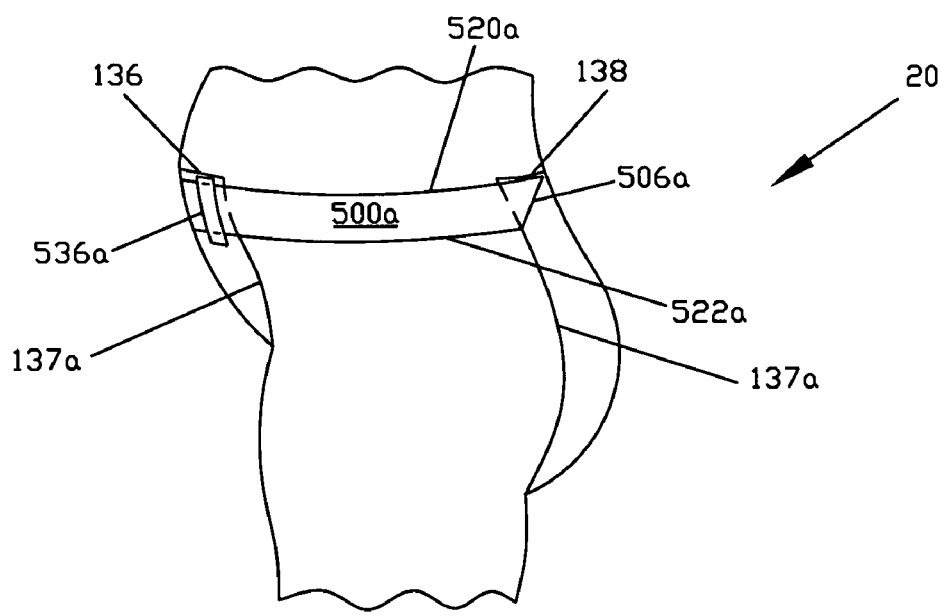
FIG. 13, FIG. 14, and FIG. 15 are respectively simplified side, front, and back elevation views of the diaper 20 of FIG. 10 being worn about the lower torso of a wearer.
Figure 14:
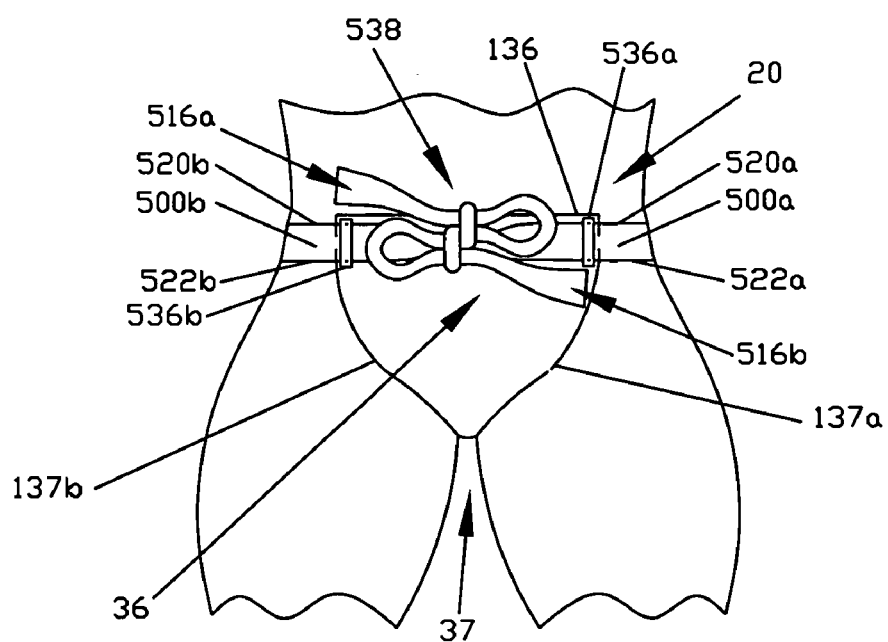
Figure 15:
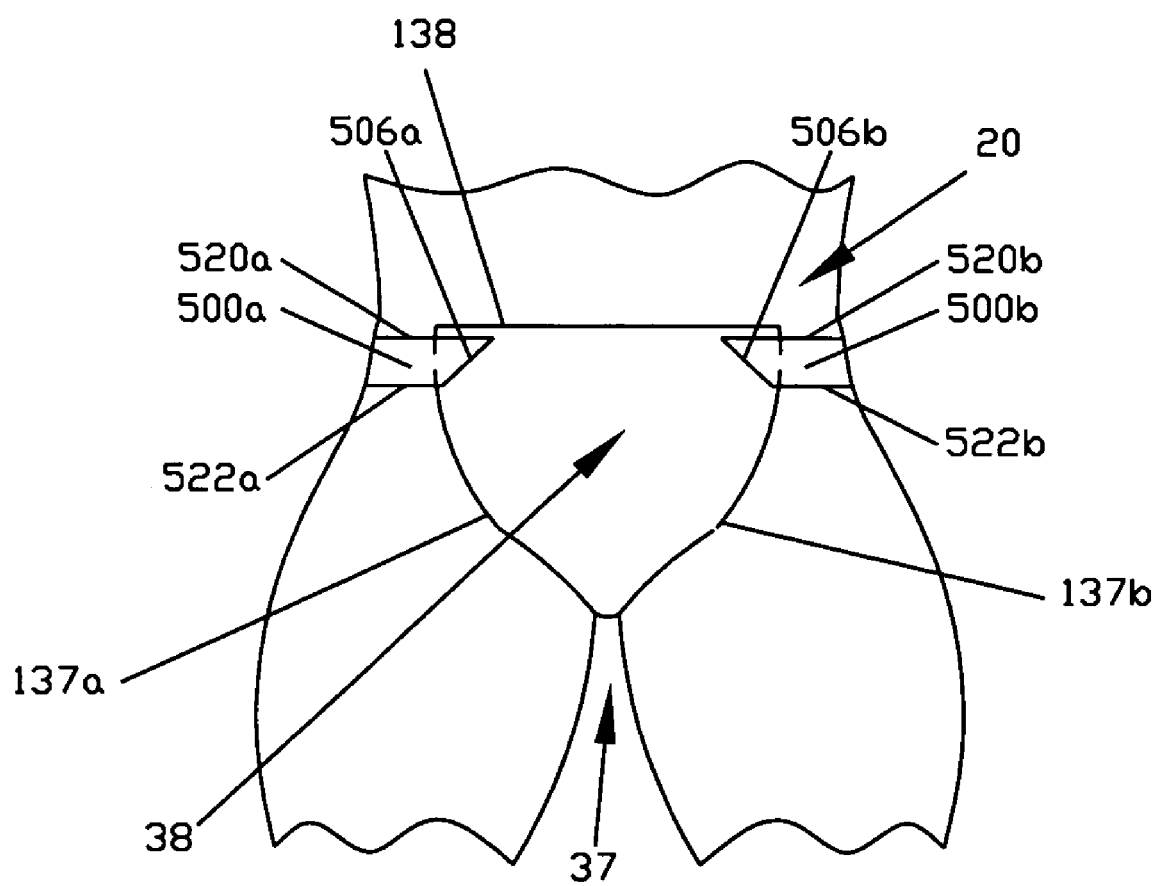

Each belt strip 500 is formed in an attached configuration as shown, for example, in FIG. 1 and in FIG. 10. The belt strip 500 is deployed for use by detaching the belt strip 500 except at its fixed end portion 507 and folding the belt strip 500 laterally outward at a diagonal fold line 506 as shown, for example, in FIG. 2 and in FIG. 11. Once deployed, each belt strip 500 is tied to another belt strip, fastened to a waist region of the diaper, and/or fastened to another belt strip in order to thereby partially or wholly encircle the waist of the wearer of the diaper 20.

In the present figures, the diagonal fold lines 506 are located adjacent to the back waist edge 138 of the diaper 20 and the belt strips 500 extend from there toward the front waist edge 136. Alternatively, the diagonal fold lines 506 may be located adjacent to the front waist edge 136 of the diaper 20, in which configuration the belt strips 500 extend toward the back waist edge 138. In general, other structural elements that are described in relation to the belt strips and whose disposition is dependent on the disposition of the belt strips may likewise be located oppositely in combination with oppositely disposed belt strips.

The belt strip 500 has a longitudinally extending first edge 520 and a laterally opposing longitudinally extending second edge 522. Each of the first and second edges is formed by either an edge of a sheet of material, a fold in a sheet of material, or a frangible separation line. The first edge 520 is located laterally proximally relative to the second edge 522 prior to the deployment of the belt strip 500 for use. When the belt strip 500 is deployed for use, the first edge 520 is positioned as the upper edge and the second edge 522 is positioned as the lower edge of the belt strip 500, i.e., the first edge 520 is disposed farther from the lateral axis 44 than the second edge 522 is disposed.

The diagonal fold line 506 has a laterally proximal end point 512 and an opposing laterally distal end point 514 located longitudinally proximally relative to the laterally proximal end point 512. In other words, the laterally distal end point 514 is located relatively closer to the lateral axis 44 of the diaper 20 than the laterally proximal end point 512 is located.

When deployed for use, the upper edge 520 of the belt strip 500 extends laterally outward from the laterally proximal end point 512 and the lower edge 522 extends laterally outward from the laterally distal end point 514. The laterally proximal end point 512 of the diagonal fold line 506 may be located at the respective waist edge or may be located below the waist edge, i.e., between the waist edge and the lateral axis 44. Thus, when the laterally proximal end point 512 is located at the waist edge, the upper edge 520 of the belt strip 500 meets the waist edge. Similarly, when the laterally proximal end point 512 is located below the waist edge, the upper edge 520 of the belt strip 500 is likewise below the waist edge.

Any portion of the chassis 100 protruding longitudinally beyond the upper edge 520 of the deployed belt strip 500 is free to fold over, either interiorly or exteriorly. Such folding over may degrade the appearance of the diaper 20 on the wearer. In addition, this folding over may negatively affect the performance of the diaper. For example, folding over into the interior may undesirably expose an exterior layer of the diaper 20, such as a plastic film, to the skin of the wearer. Conversely, folding over to the exterior may expose a wet interior layer of the diaper 20 to clothing or bedding. Therefore, it may be desirable to locate the laterally proximal end point 512 at or closely adjacent to the waist edge in order to minimize the size of any such portion of the chassis 100 protruding longitudinally beyond the upper edge 520 of the deployed belt strip 500 and thereby prevent, or at least minimize, the magnitude of any degradation in appearance and/or performance.

For the purpose of clarity in the present drawing figures, the laterally proximal end point 512 of each deployed belt strip 500 and the upper edge 520 of that deployed belt strip 500 are shown displaced slightly from the back waist edge 138 of the diaper 20, rather than being shown exactly coincident with that waist edge. This depiction is intended to represent the preference that the upper edge 520 of the deployed belt strip 500 be located either at or closely adjacent to the waist edge in order to minimize the protrusion of the chassis 100 beyond the upper edge 520, for the reason explained above. In order to locate the upper edge 520 as preferred, the distance between the laterally proximal end point 512 and the closest waist edge is less than the longitudinal distance between the laterally proximal end point 512 and the laterally distal end point 514. For example, the laterally proximal end point 512 may be located within approximately 6 mm of the closest waist edge of the diaper 20.

The diagonal fold line 506 may be oriented such that a deployed belt strip 500 extends parallel to the lateral axis 44 or at an angle with respect to the lateral axis 44. For example, a belt strip 500 formed parallel to the longitudinal axis 42 and deployed by being folded laterally outward at a fold line 506 oriented at 45 degrees to both the longitudinal axis 42 and the lateral axis 44 of the diaper 20 extends parallel to the lateral axis 44 when deployed. However, when such a longitudinally parallel formed belt strip 500 is folded at a fold line 506 oriented at an angle other than 45 degrees, the belt strip 500 extends at an angle with respect to the lateral axis 44. Similarly, a belt strip 500 formed at an angle relative to the longitudinal axis 42 and deployed by being folded laterally outward at a 45 degree diagonal fold line 506 extends at an angle with respect to the lateral axis 44. For example, in some embodiments, it may be desirable to fit the deployed belt strip 500 on the torso of a wearer along a path running from the small of the back to below the navel.

In its fixed end portion 507, the belt strip 500 is attached to another layer of the diaper 20 at both the laterally proximal end point 512 and the laterally distal end point 514 of the diagonal fold line 506 in an attachment zone 508. The attachment zone 508 may have a continuous or intermittent form, for example two points, a pattern of more than two points, a continuous area, or a pattern of discontinuous areas. Thus, the belt strip 500 may be attached either continuously or intermittently along the diagonal fold line 506 between the laterally proximal end point 512 and the laterally distal end point 514. The attachment zone 508 may be formed by any means suitable for the materials involved, including stitching, adhesive bonding, thermal bonding, stapling, and riveting, for example.

For example, as shown in FIG. 1 and in FIG. 10, the attachment zone 508 may extend longitudinally and laterally outward from the diagonal fold line 506 in directions away from both the longitudinal axis 42 and the lateral axis 44. Such a triangular attachment zone 508 may be desirable in order to strengthen and/or stabilize this area where any force exerted by a deployed belt strip 500 is transmitted to the remainder of the structure of the diaper 20.

Figure 7:
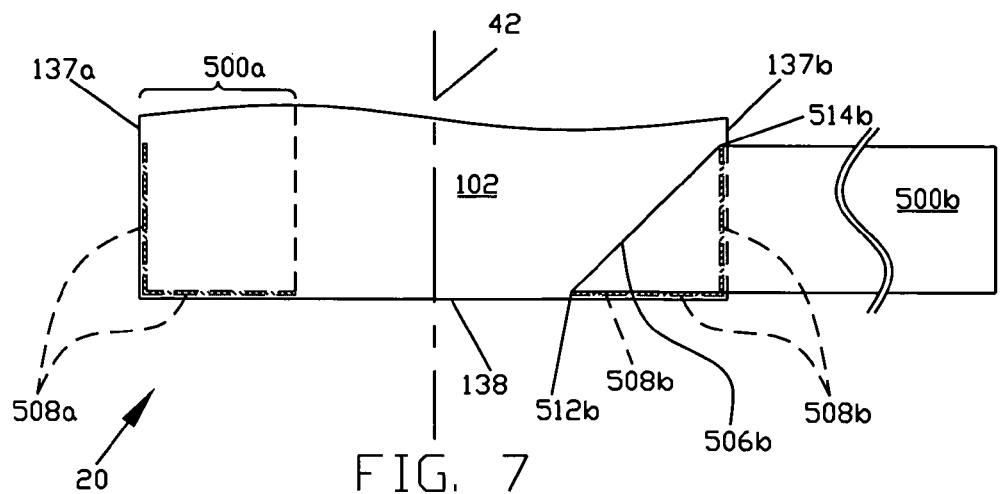
FIG. 7, FIG. 8, and FIG. 9 are plan views of portions of exemplary diapers 20 showing alternative attachment patterns 508.
Figure 8:
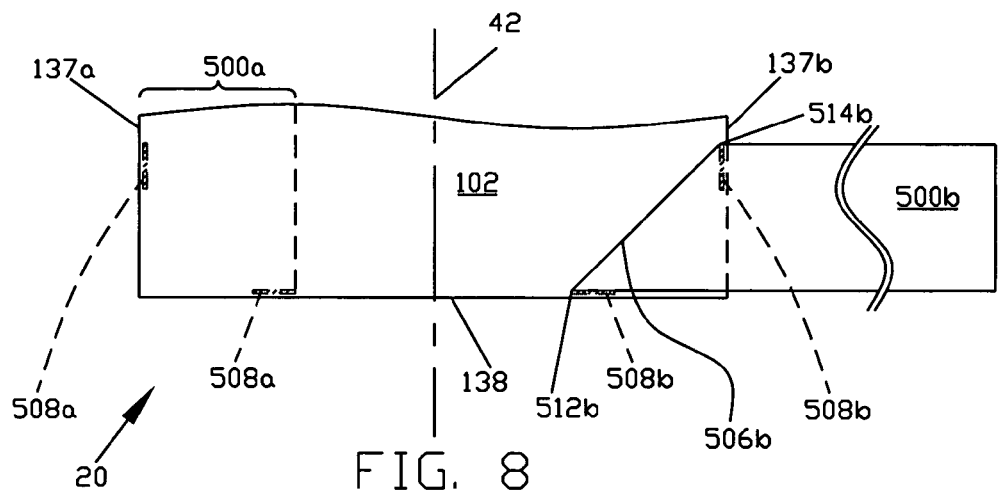
Figure 9:
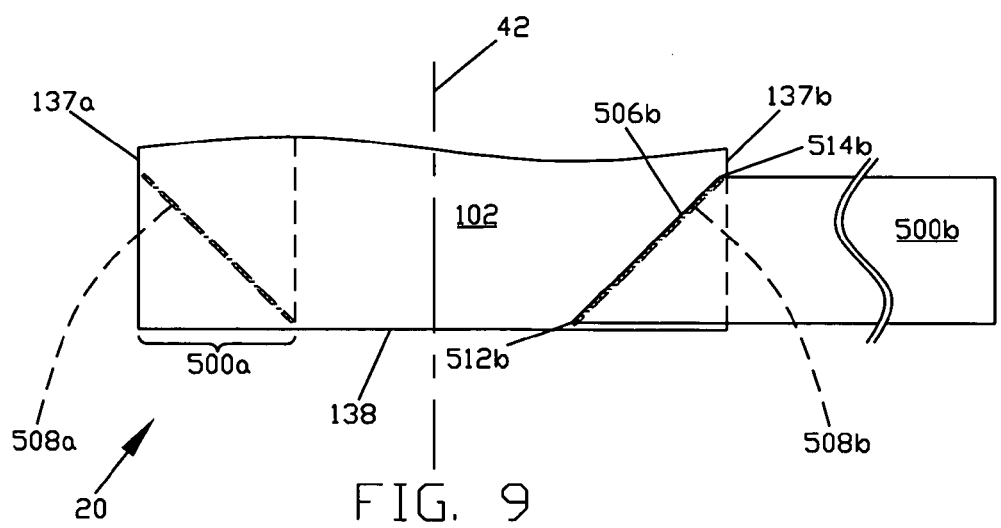
Figure 16:
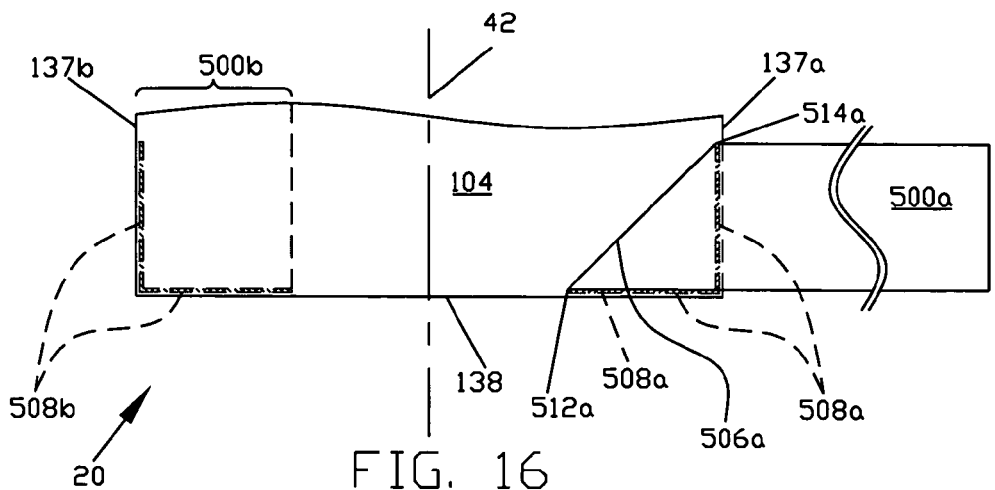
FIG. 16, FIG. 17, and FIG. 18 are plan views of portions of exemplary diapers 20.
Figure 17:
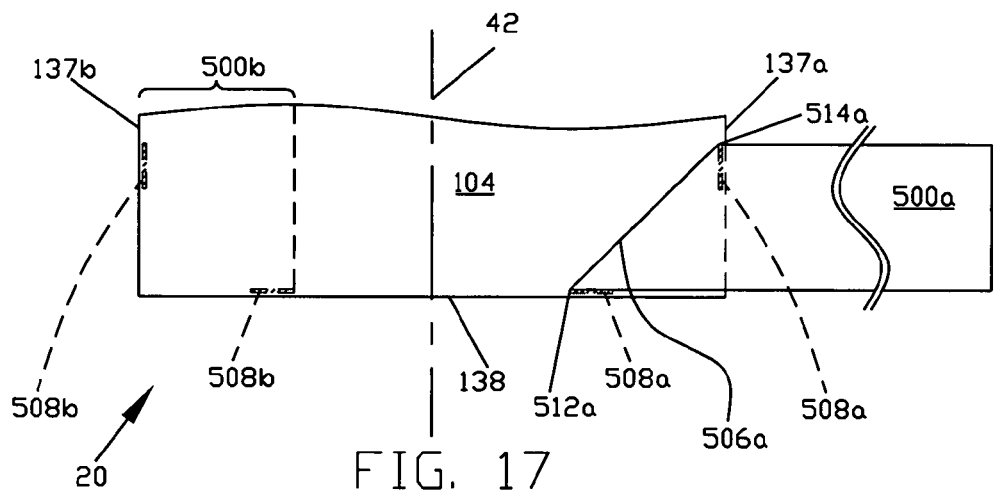
Figure 18:
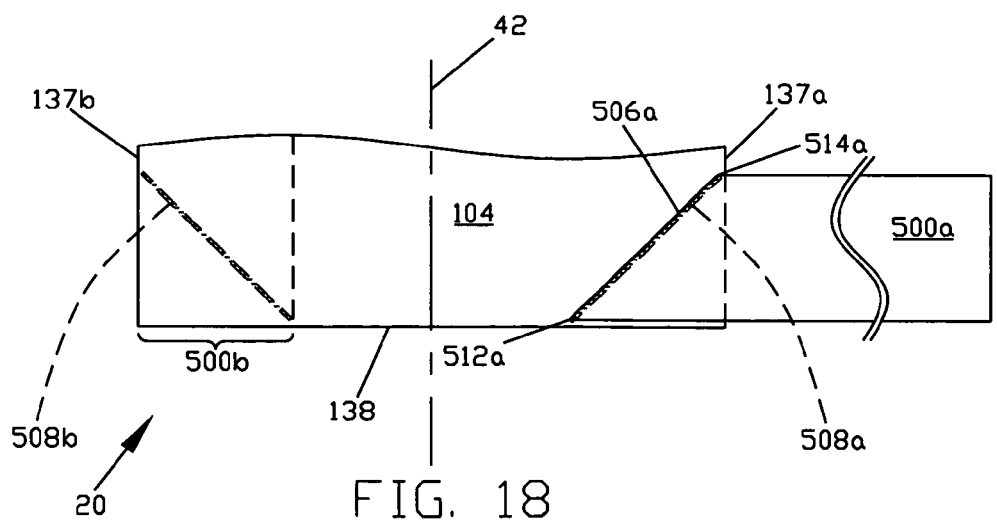

As other examples, as shown in FIG. 7 and FIG. 8 and in FIG. 16 and FIG. 17, the attachment zone 508 may extend longitudinally from the laterally distal end point 514 of the diagonal fold line 506 in a direction away from the lateral axis 44 toward or to the adjacent waist edge of the diaper 20 and laterally from the laterally proximal end point 512 of the diagonal fold line 506 in a direction in a direction away from the longitudinal axis 42 toward or to the adjacent side edge of the diaper 20, without forming a triangle. As yet another example, as shown in FIG. 9 and in FIG. 18, the attachment zone 508 may extend from the laterally proximal end point 512 toward or to the laterally distal end point 514 along the diagonal fold line 506 itself.

Because the belt strip 500 is attached at least at both ends of the diagonal fold line 506, any tension in the belt strip 500 is transmitted to the remainder of the structure of the diaper 20 over the width of the belt strip 500, rather than being concentrated at a single point. Such a distributed transmission of force may be desirable in order to minimize the possibility of marking the skin of the wearer and/or to minimize the possibility of overstressing the structure. In particular, when the belt strip 500 is attached along the entire diagonal fold line 506 or in a triangular attachment zone 508 as described above, the tensile force may be uniformly distributed across the width of the belt strip 500.

Figure 19:
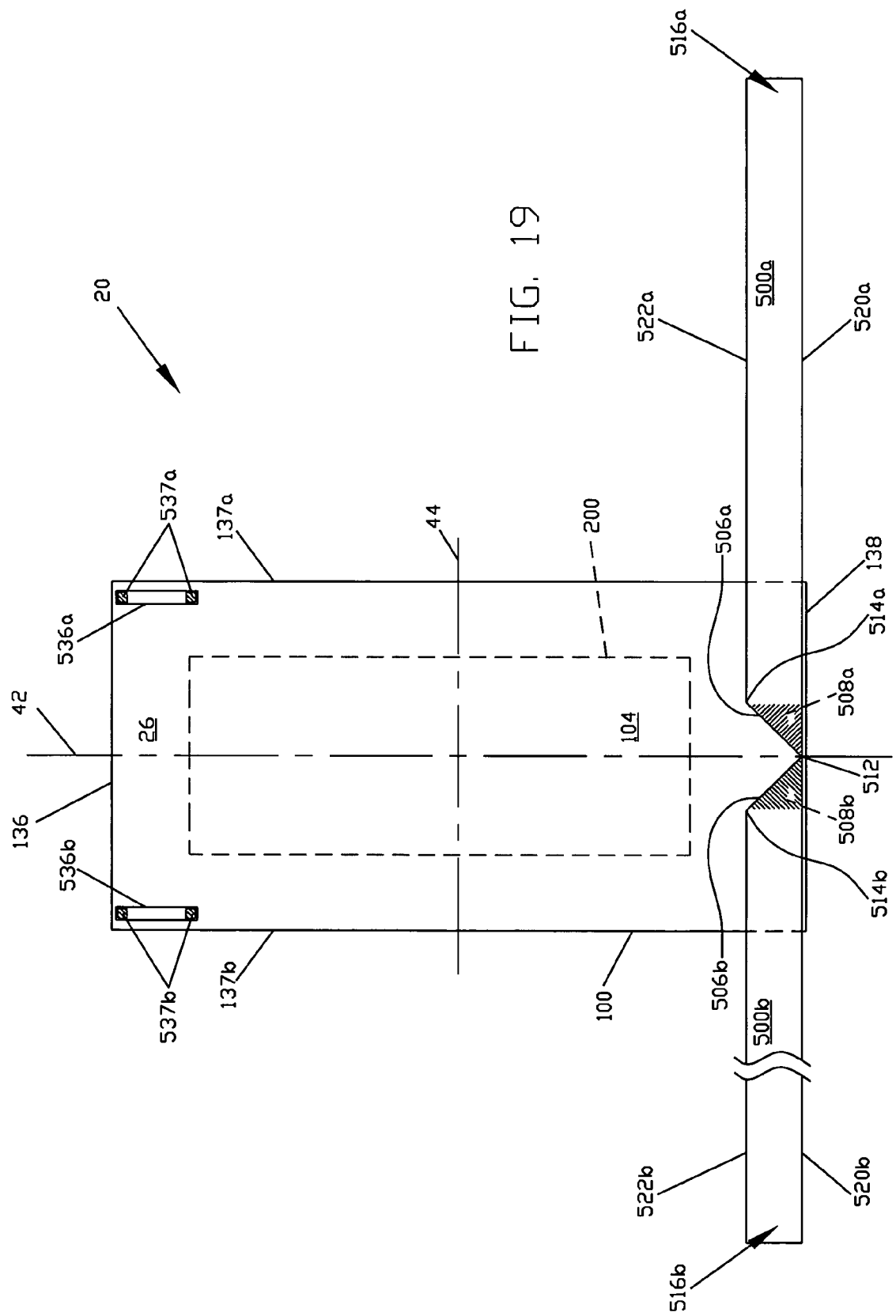
FIG. 19 is an exterior plan view of another exemplary disposable diaper 20.
Figure 20:
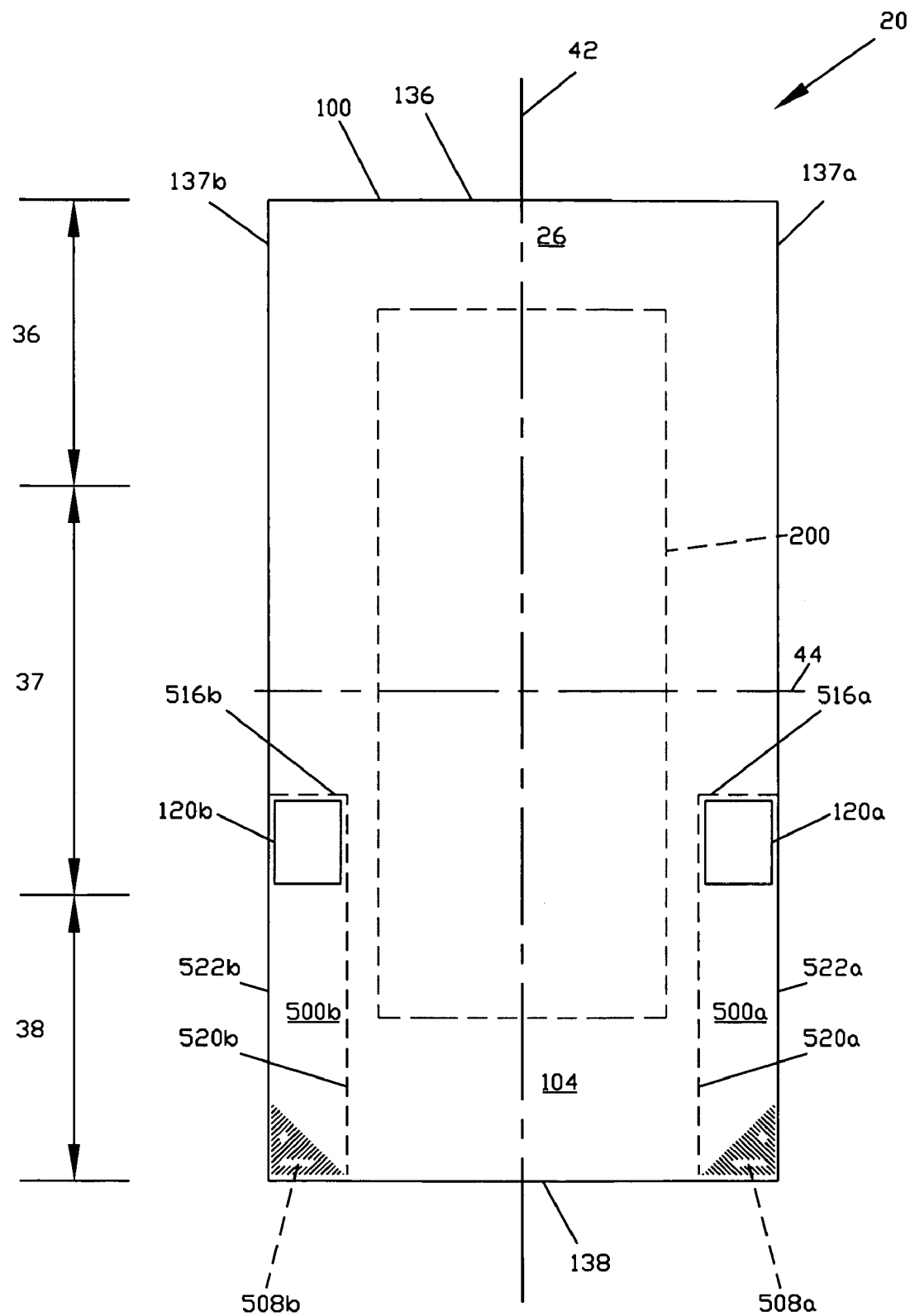
FIG. 20 is an exterior plan view of another exemplary disposable diaper 20.
Figure 21:
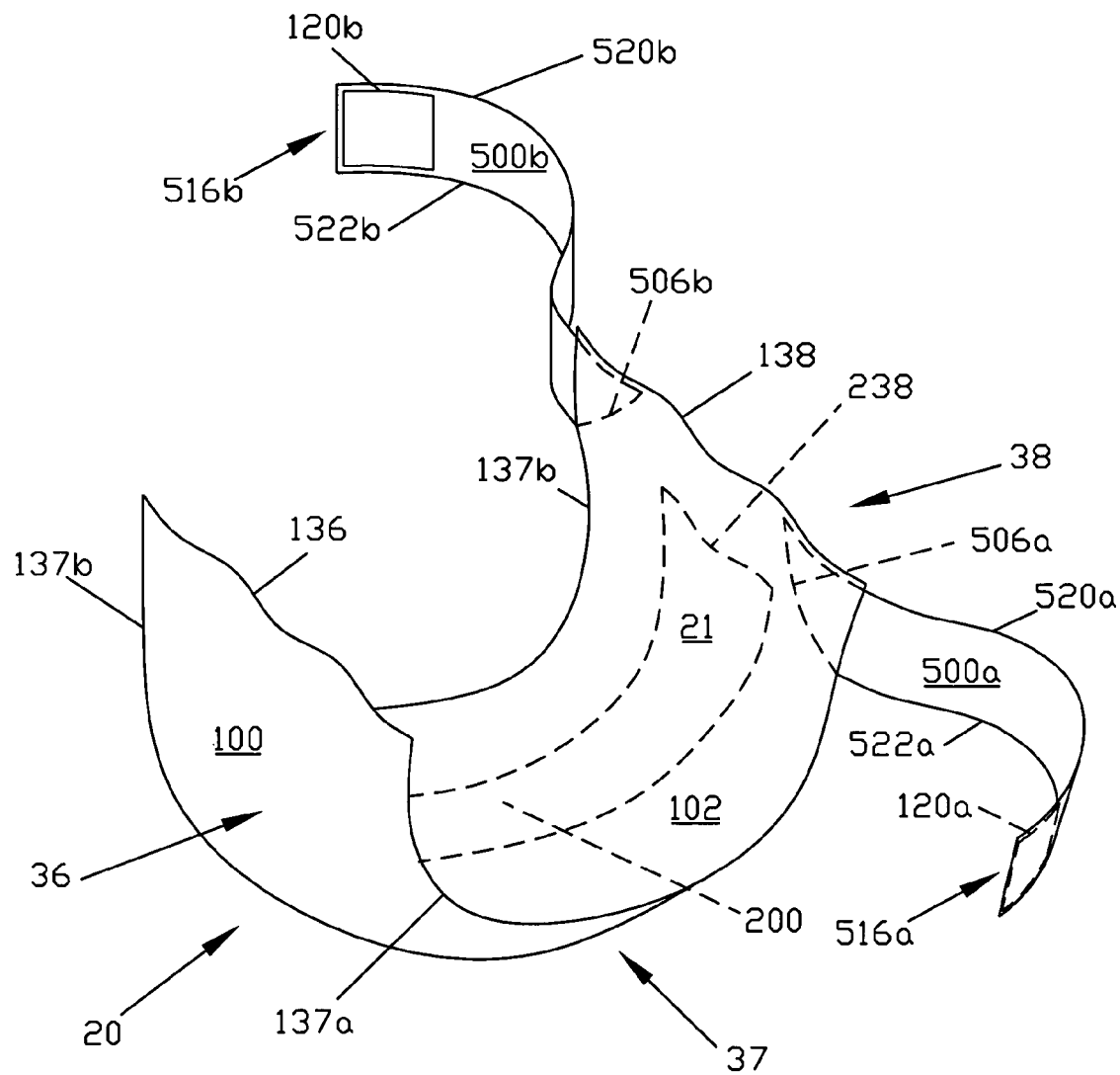
FIG. 21 is a perspective view of the diaper 20 of FIG. 20 showing the belt strips 500 deployed.

In FIG. 1 through FIG. 18, the diaper 20 has two belt strips 500 that are laterally spaced apart. Alternatively, two belt strips 500 may be laterally abutted, rather than being spaced apart. For example, in FIG. 19, the two belt strips 500 are disposed such that their respective first edges 520 extend from a common laterally proximal end point 512 of both of their diagonal fold lines 506. Thus, prior to deployment, these two belt strips 500 had a common first edge 520 extending from the common laterally proximal end point 512. In FIG. 19, the two belt strips 500 are disposed symmetrically with respect to the longitudinal axis 42 of the diaper 20. Alternatively, two laterally abutted belt strips 500 may be disposed asymmetrically with respect to the longitudinal axis 42 of the diaper 20.

Prior to deployment for use, each belt strip 500 may extend from the laterally proximal end point 512 of the diagonal fold line 506 to the opposing waist edge. For example, in FIG. 1 and in FIG. 10, each belt strip 500 extends from its laterally proximal end point 512 located adjacent to the back waist edge 138 to the opposing front waist edge 136. When such a "full length" belt strip 500 is deployed for use, a portion of the opposing waist edge defines a free end portion 516 of the belt strip 500, as shown in FIG. 2, FIG. 3, FIG. 11, and FIG. 12.

Figure 22:
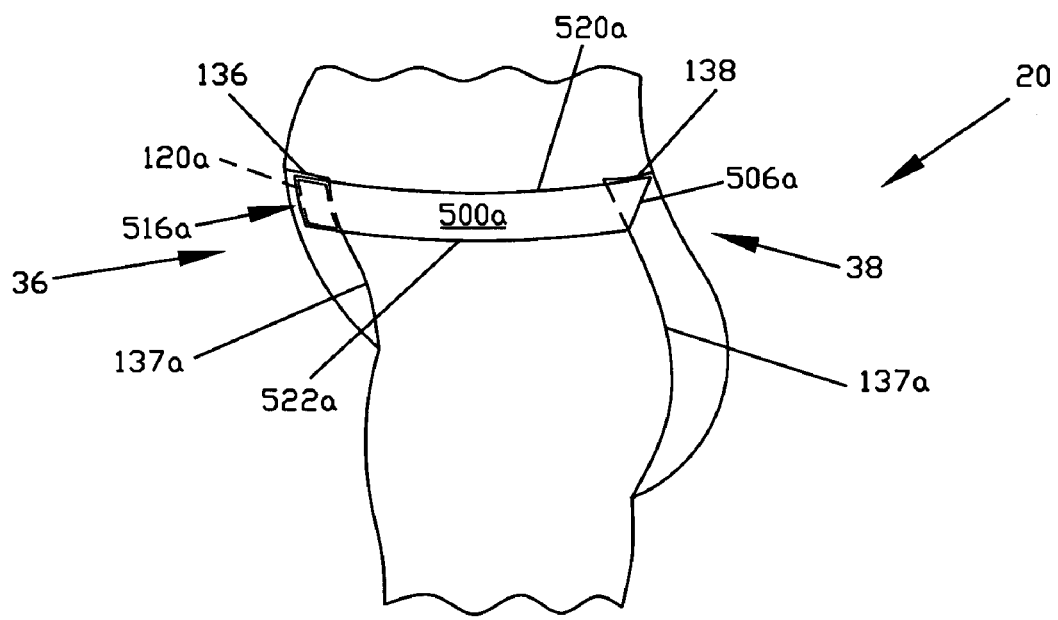
FIG. 22 and FIG. 23 are respectively simplified side and front elevation views of the diaper 20 of FIG. 20 being worn about the lower torso of a wearer.
Figure 23:
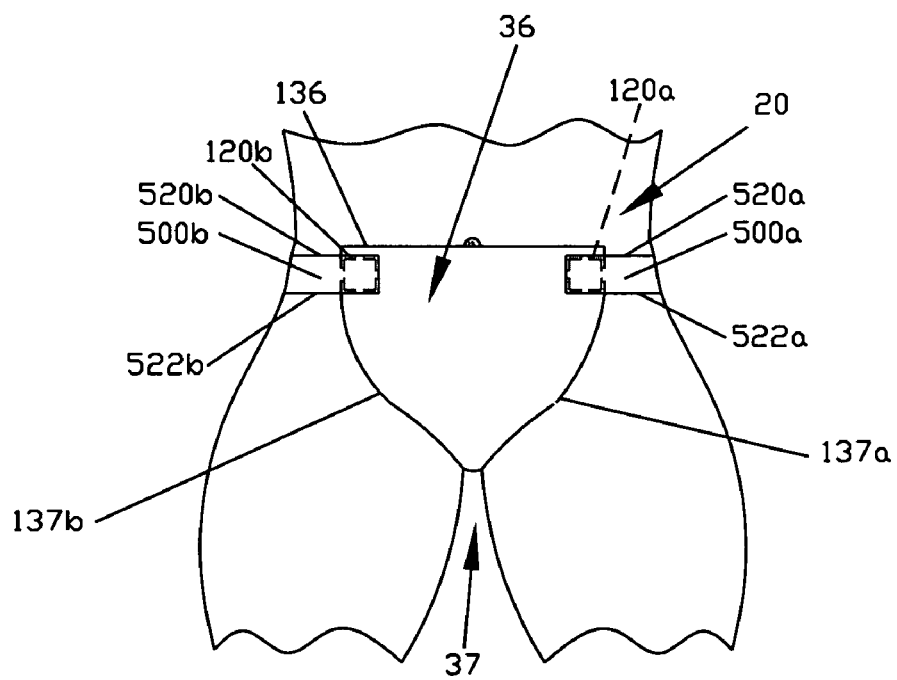

Alternatively, the belt strip 500 may extend only a part of the way between the laterally proximal end point 512 and the opposing waist edge. For example, in FIG. 20 and in FIG. 21, each belt strip 500 extends from its laterally proximal end point 512 located adjacent to the back waist edge 138 to a free end portion 516 located between the laterally proximal end point 512 and the opposing front waist edge 136. This free end 516 may be defined by a laterally extending frangible separation line. As shown in FIG. 22 and FIG. 23, when the diaper 20 is applied onto the wearer, each such partial length belt strip 500 may be used to connect the waist regions at and/or adjacent to a respective side edge of the diaper 20. Such laterally opposing partial length belt strips 500 may overlap or may end short of overlapping.

Figure 24:
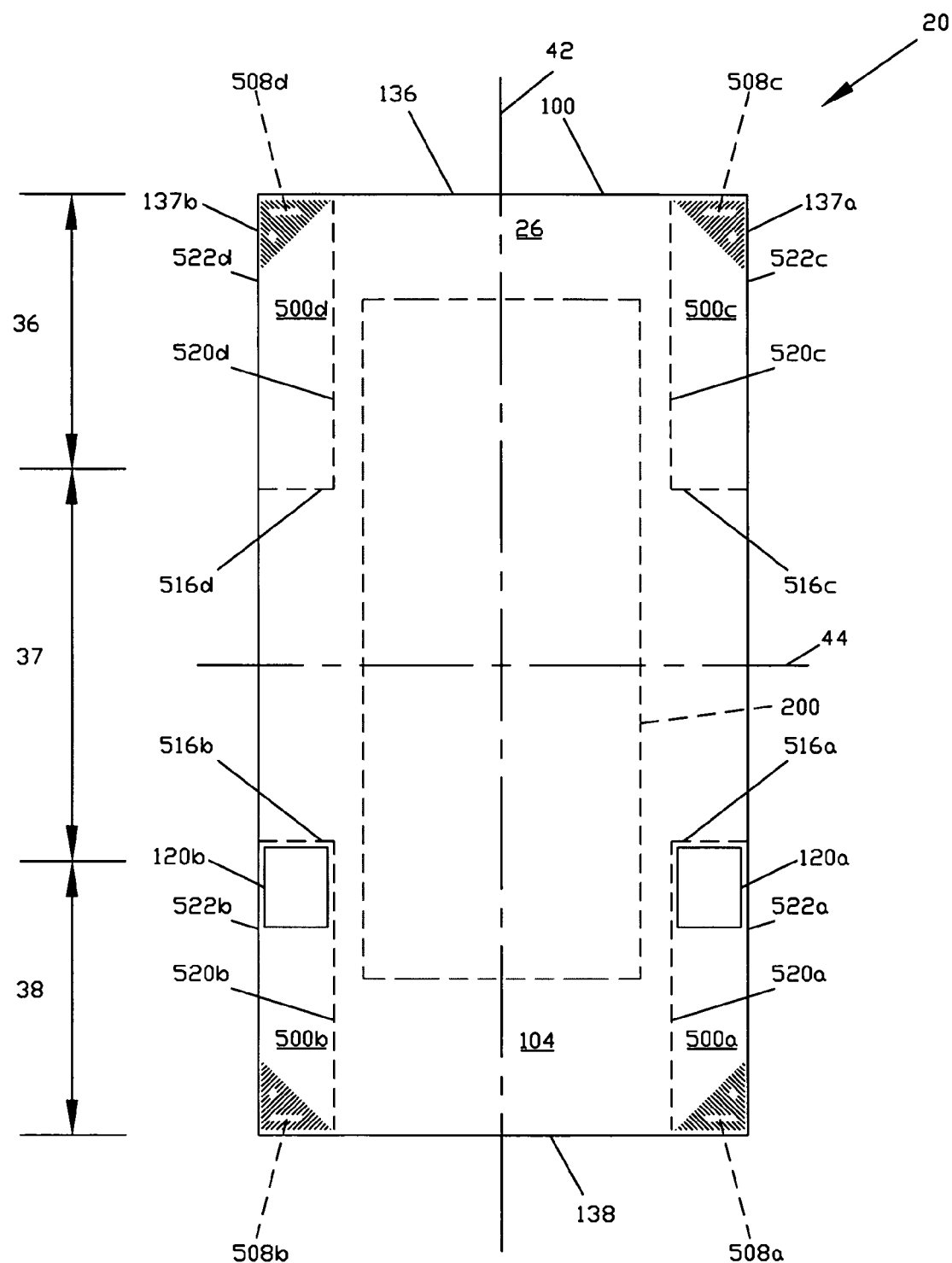
FIG. 24 is an exterior plan view of another exemplary disposable diaper 20.
Figure 25:
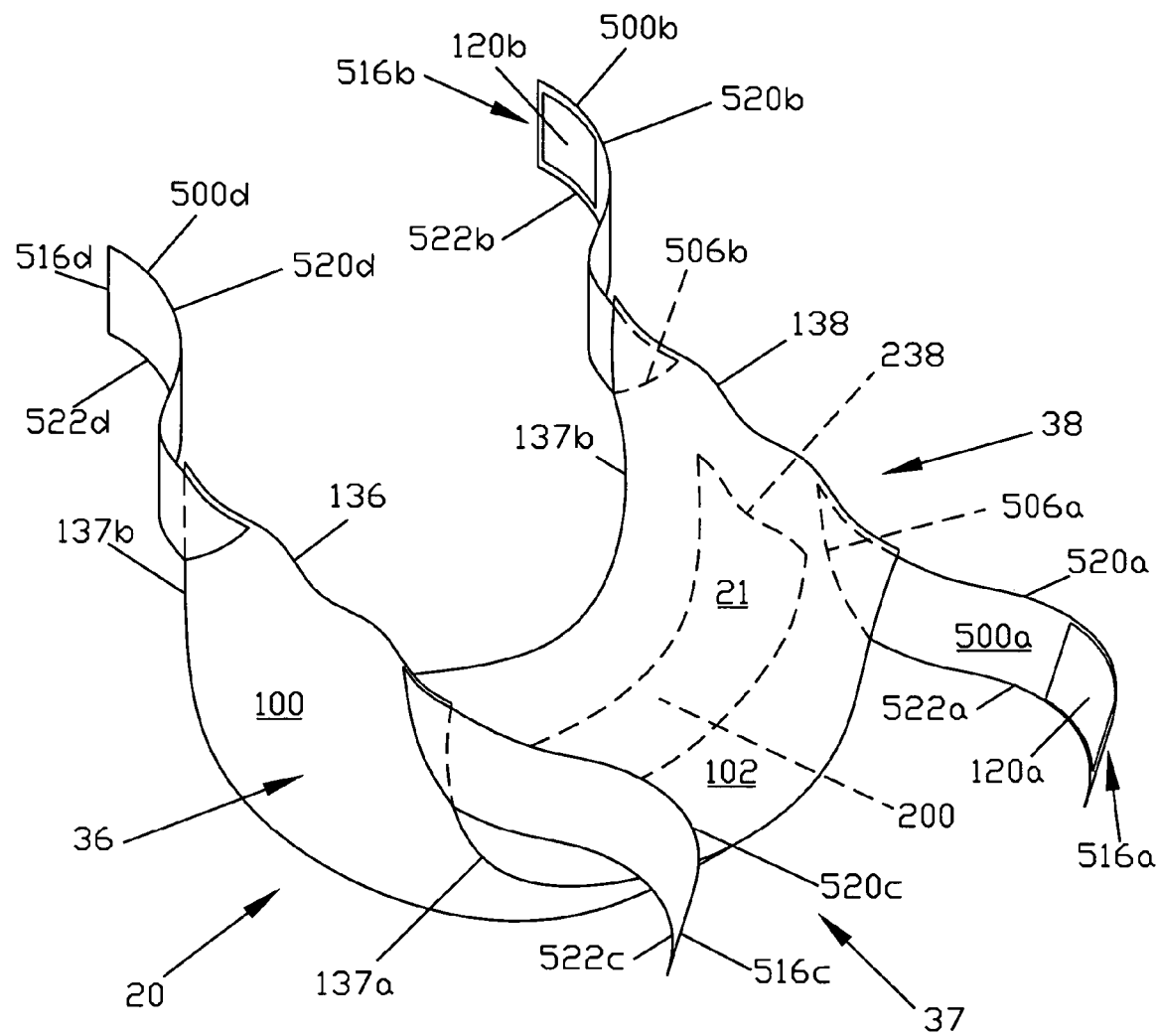
FIG. 25 is a perspective view of the diaper 20 of FIG. 24 showing the belt strips 500 deployed.
Figure 26:
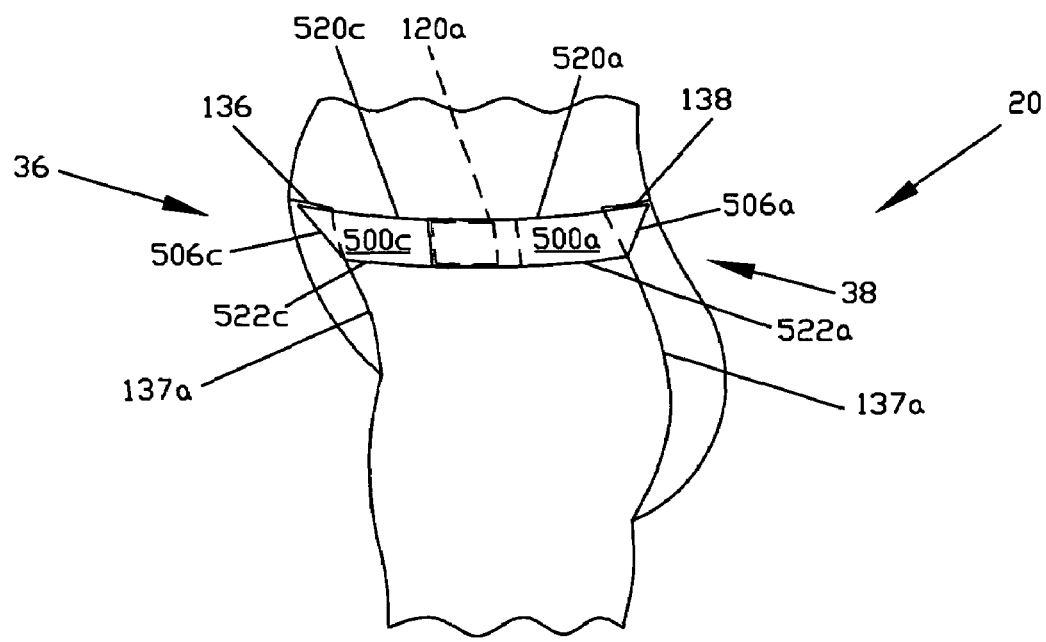
FIG. 26 and FIG. 27 are respectively simplified side and front elevation views of the diaper 20 of FIG. 24 being worn about the lower torso of a wearer.
Figure 27:
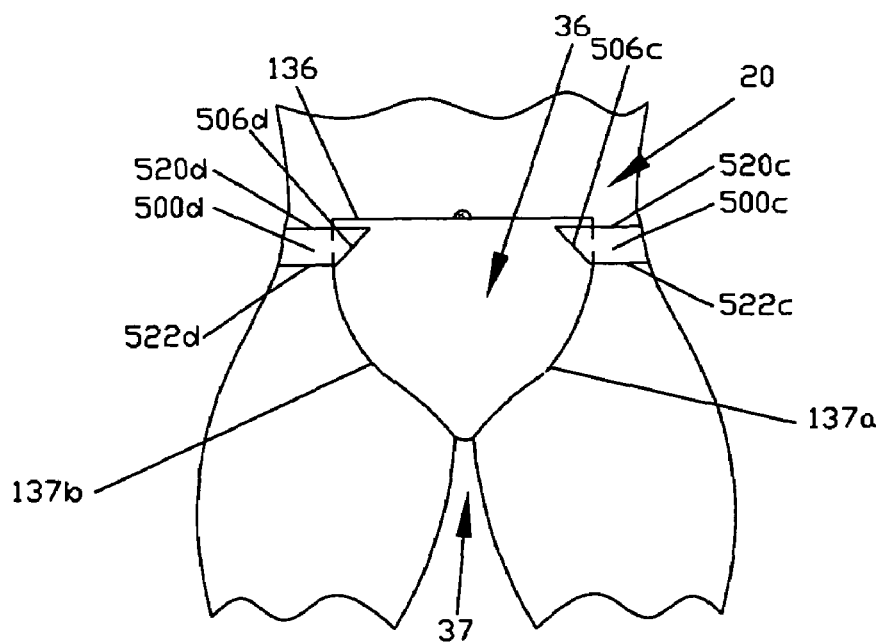

As another alternative, as shown in FIG. 24 and in FIG. 25, two longitudinally opposing partial length belt strips 500 may be formed adjacent to each side edge of the diaper 20, for a total of four belt strips 500. When the diaper 20 is applied onto the wearer, the two laterally opposing partial length belt strips 500c and 500d in the front waist region 36 and the respective laterally opposing partial length belt strips 500a and 500b in the back waist region 38 are used to connect the waist regions at and/or adjacent to the respective side edges of the diaper 20 as shown in FIG. 26 and in FIG. 27. In particular, the partial length belt strips 500a and 500c adjacent to the left side edge 137a are attached together and the partial length belt strips 500b and 500d adjacent to the right side edge 137b are attached together.

Figure 28:
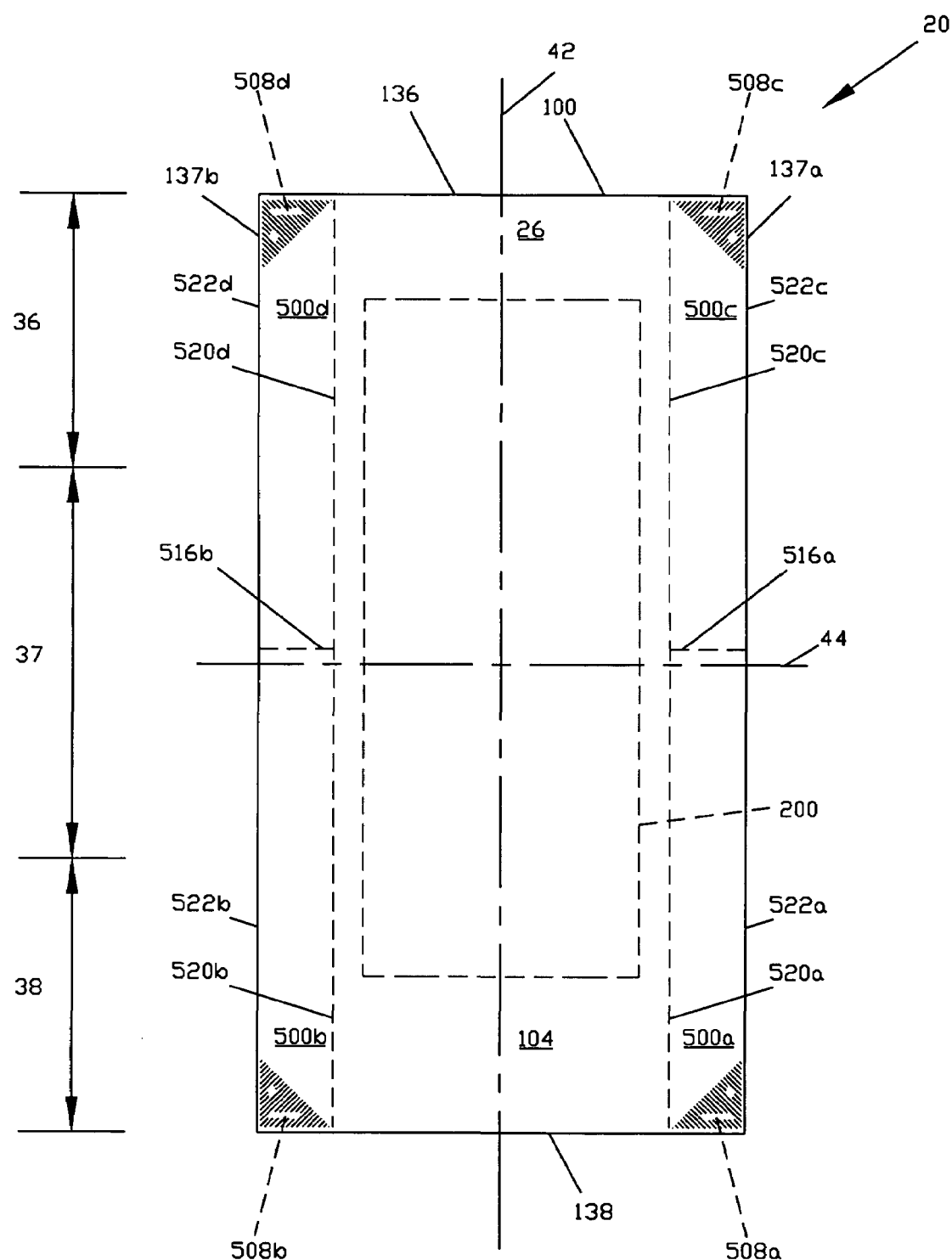
FIG. 28 is an exterior plan view of another exemplary disposable diaper 20.
Figure 29:
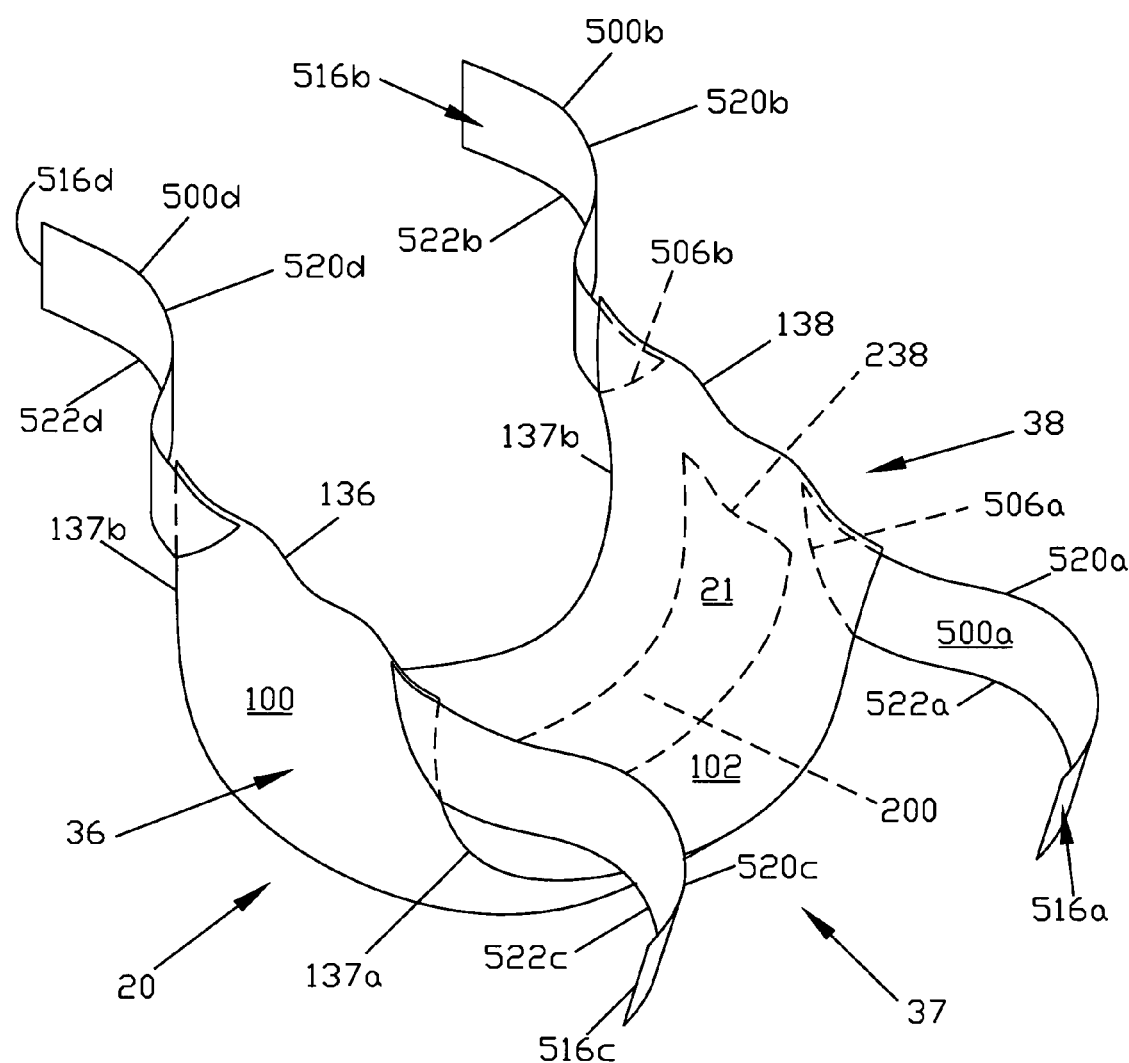
FIG. 29 is a perspective view of the diaper 20 of FIG. 28 showing the belt strips 500 deployed.
Figure 30:
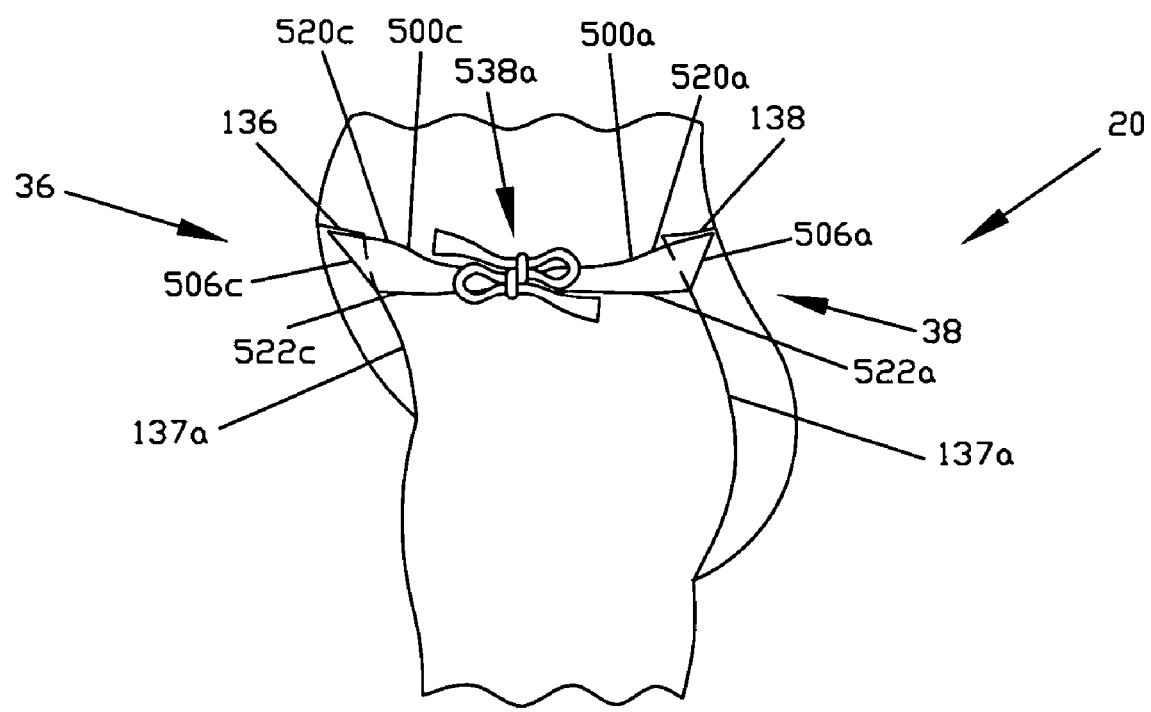
FIG. 30 is a simplified side elevation view of the diaper 20 of FIG. 28 being worn about the lower torso of a wearer.

As shown in FIG. 24, the two longitudinally opposing partial-length belt strips 500 on each side may not meet. As an alternative, as shown in FIG. 28 and in FIG. 29, the two longitudinally opposing partial length belt strips 500 on each side may meet at their free end portions 516, thereby being relatively longer than in a configuration in which they do not meet, and may be long enough to be tied together, as shown in FIG. 30.

Figure 31:
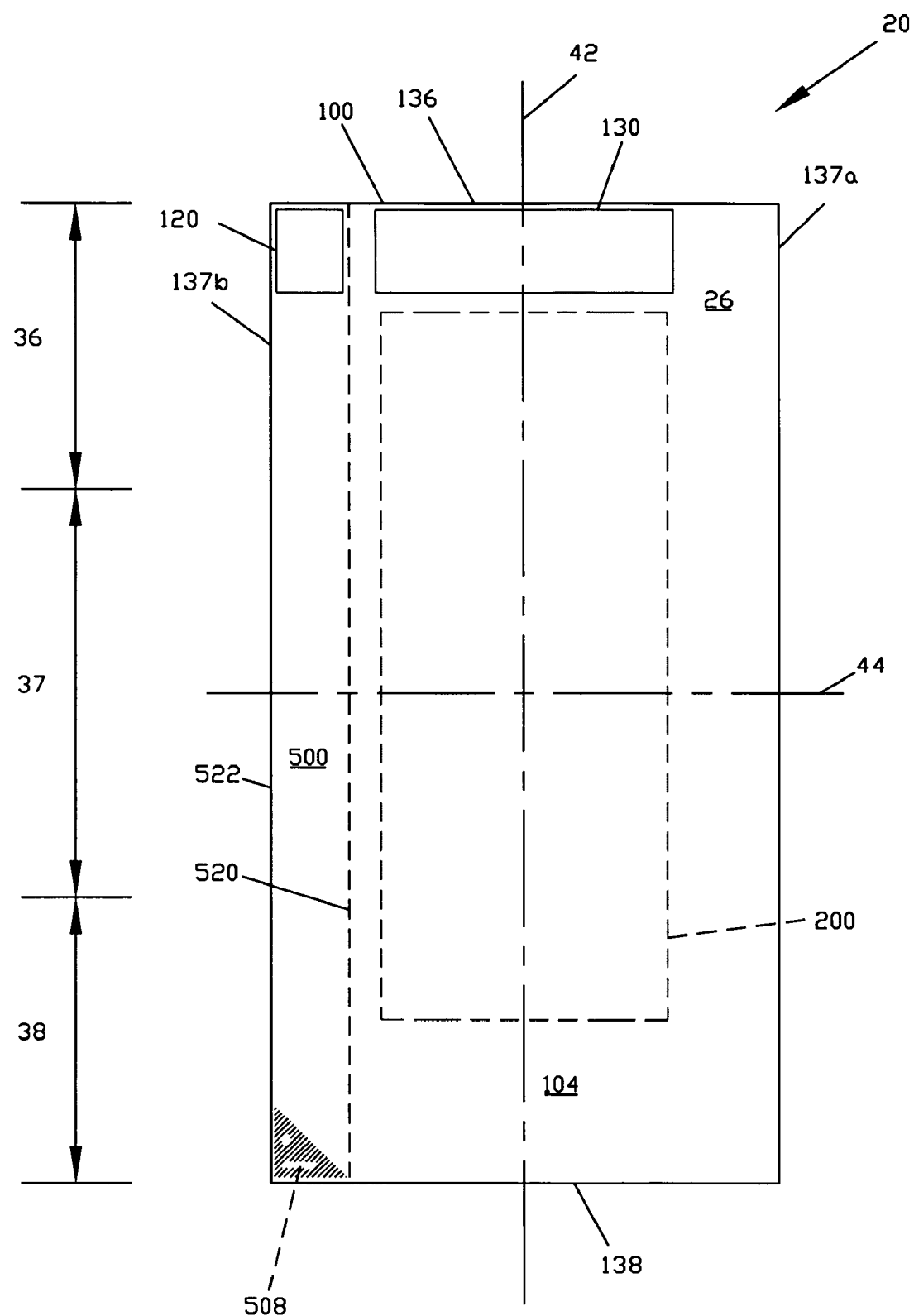
FIG. 31 is an exterior plan view of another exemplary disposable diaper 20.
Figure 32:
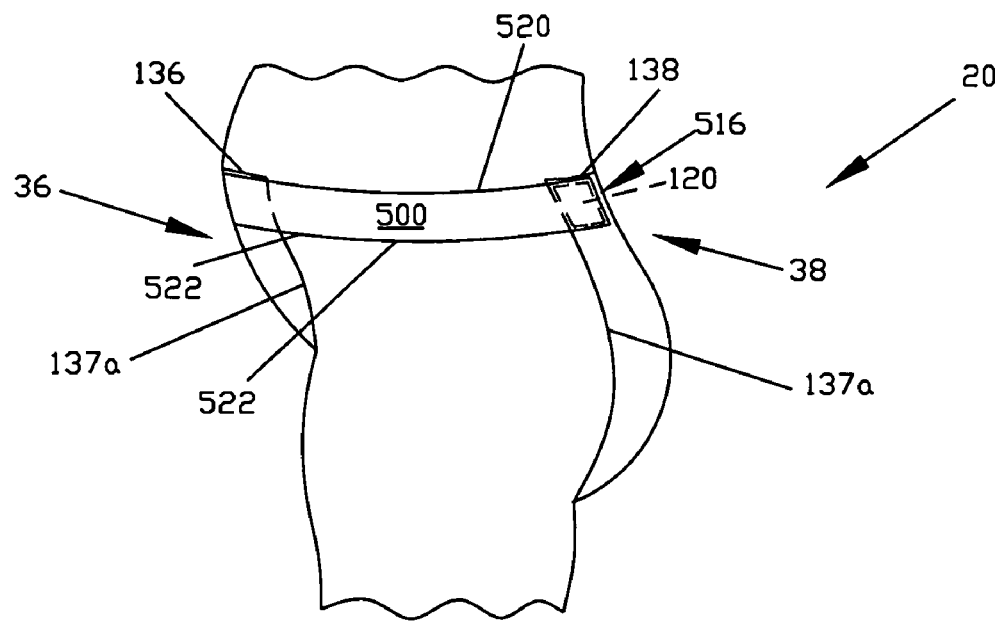
FIG. 32, FIG. 33, and FIG. 34 are respectively simplified side, front, and back elevation views of the diaper 20 of FIG. 31 being worn about the lower torso of a wearer.
Figure 33:
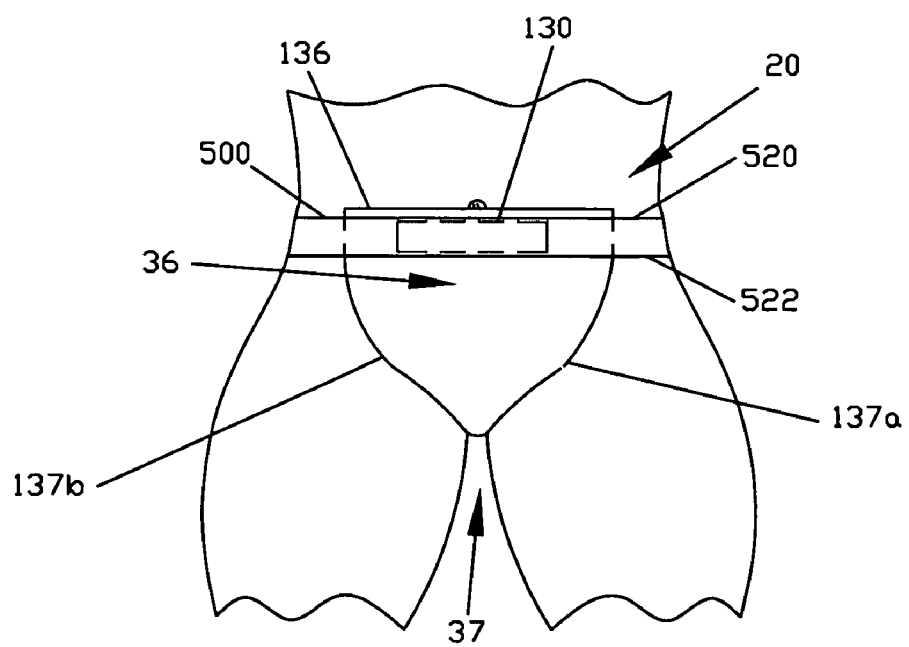
Figure 34:
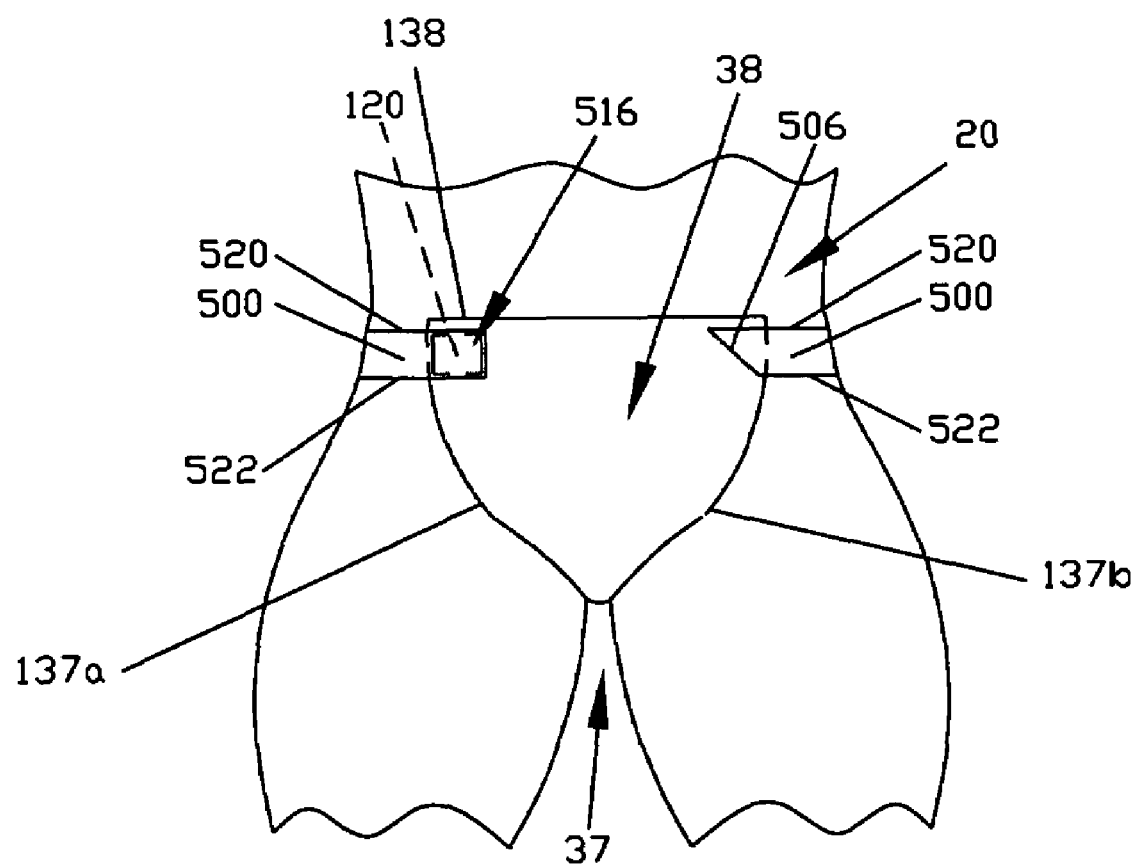

As another alternative, as shown in FIG. 31 through FIG. 34, the diaper 20 may have only a single deployable belt strip 500. When the diaper 20 is applied onto the wearer, such a "full length" belt strip 500 may be long enough to extend across the entirety of the opposing waist region and back to the starting waist region. In other words, a single full length belt strip 500 may be used to connect the waist regions at and/or adjacent to both of the side edges of the diaper 20. For example, as shown in FIG. 32, FIG. 33, and FIG. 34, the single belt strip 500 in FIG. 31 extends from the diagonal fold line 506 adjacent to the right side edge 137b in the back waist region 38 across the front waist region 36 and to the back waist region 38 such that its free end portion 516 lies adjacent to the left side edge 137a in the back waist region 38.

As shown in FIG. 5, FIG. 6, FIG. 14, and FIG. 30, two deployed belt strips 500 may be tied together in a knot 538 when they are long enough to make this practical. Alternatively, a fastener may be used to attach two deployed belt strips 500 together. Prior to fastening, the fastener may be disposed on either of the two belt strips 500. For example, in FIG. 26, the fastener 120a is used to attach the back left belt strip 500a to the front left belt strip 500c and the fastener 120b is similarly used to attach the back right belt strip 500b to the front right belt strip 500d. Alternatively, complementary fasteners may be disposed on matching belt strips 500, e.g., a hook patch may be disposed on one belt strip and a complementary loop patch may be disposed on another belt strip such that the two belt strips may be fastened together.

Alternatively, a fastener may be used to attach a deployed belt strip 500 to another portion of the diaper 20. Prior to fastening, the fastener may be disposed on the belt strip 500 or may be disposed on the other portion of the diaper 20 to which the belt strip 500 is to be fastened. For example, in FIG. 22 and FIG. 23, each fastener 120 is used to attach the respective belt strip 500 to the front waist region 36 of the diaper 20. As another example, in FIG. 32 and FIG. 34, the single fastener 120 is used to attach the single belt strip 500 to the back waist region 38. Alternatively, complementary fasteners may be used, e.g., a hook patch may be disposed on a belt strip and a complementary loop patch may be disposed on the other portion of the diaper 20 to which the belt strip is to be fastened.

The fastener 120 may be any type of fastening device suitable for the materials involved, for example an adhesive fastener, a cohesive fastener, a hook, a loop, a button, a patch of hooks, a patch of loops, etc. A fastener in the form of a patch of hooks that engage a nonwoven material may be suitable in some embodiments. The fastening of the belt strip 500 may become permanent once it is made, such that it cannot be undone without damage to the structural elements involved. Alternatively, the fastening of the belt strip 500 can be releasable and refastenable, such that it can be released for adjustment or for inspection of the interior of the diaper 20 and then refastened as before. The belt strip 500 may be fastened and/or tied at and/or adjacent to its free end portion 516. Alternatively or in addition, the belt strip 500 may be fastened and/or tied at one or more intermediate points between the diagonal fold line 506 and the free end portion 516.

When a deployed belt strip 500 is attached to a waist region by a fastener 120 or when two deployed belt strips 500 are tied or fastened together at a side of the body as in FIG. 30, both waist regions of the diaper 20 will be supported by the belt strips 500 that are attached to them. However, when two deployed belt strips 500 are tied together over a waist region to which they are not attached, as in FIG. 5 and in FIG. 14, or when a deployed belt strip 500 passes completely across a waist region to which it is not attached, as in FIG. 33, that waist region may tend to slide downward, i.e., toward the crotch region 37, relative to the belt strip 500, depending on the coefficients of static and dynamic friction between the waist region and the belt strip 500. In some embodiments, this inherent friction may be sufficient to prevent relative movement. Alternatively, it may be necessary and/or desirable to supplement such inherent friction in order to ensure that the waist region will not slide downward.

For example, in FIG. 1 through FIG. 5, in FIG. 10 through FIG. 14, and in FIG. 19, the belt strips 500 pass through laterally spaced belt loops 536, each of which is attached to the front waist region 36. Each belt loop 536 transfers force from the waist region to the belt strip 500 and thereby supports the front waist region 36 from the belt strip 500. The belt loops 536 may be attached to the waist region by any means suitable for the materials involved, including stitching, adhesive bonding, thermal bonding, stapling, and riveting, for example. For example, the belt loops 536 in the present figures are shown attached in attachment zones 537.

Figure 35:
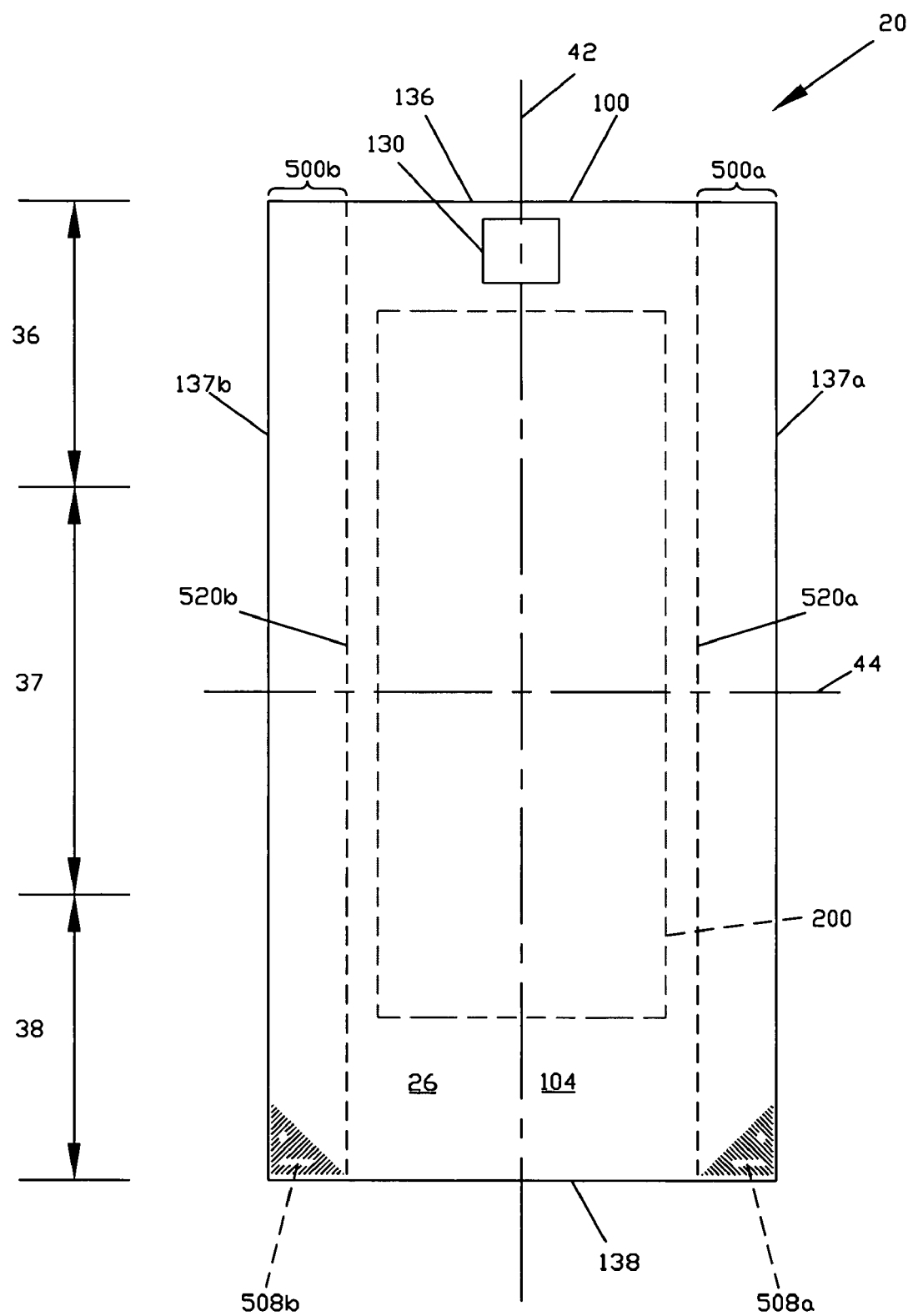
FIG. 35 is an exterior plan view of another exemplary disposable diaper 20.

Optionally, as shown in FIG. 31 FIG. 33, and FIG. 35, an additional fastener 130 similar to any of the fasteners 120 described above may be disposed on the front waist region 36, where it will be overlapped by a belt strip 500, in order to transfer force from the waist region to the belt strip 500 and thereby support the waist region from the belt strip 500. Such a fastener may be disposed on the belt strip 500, instead of on the chassis 100 as shown. A suitable fastener may be relatively wide as shown in FIG. 31 and FIG. 33 or relatively narrow as shown in FIG. 35 and may have any shape, such as the rectangular shape shown in these figures. As an alternative to a fastener, a friction patch having a relatively high coefficient of static friction may be used. The fastener or friction patch may be disposed such that the belt strip may be overlapped exteriorly of the waist region, as shown in the figures. Alternatively, the fastener or friction patch may be disposed such that the belt strip lies against the body of the wearer and the waist region is overlapped exteriorly of the belt strip.

Figure 36:
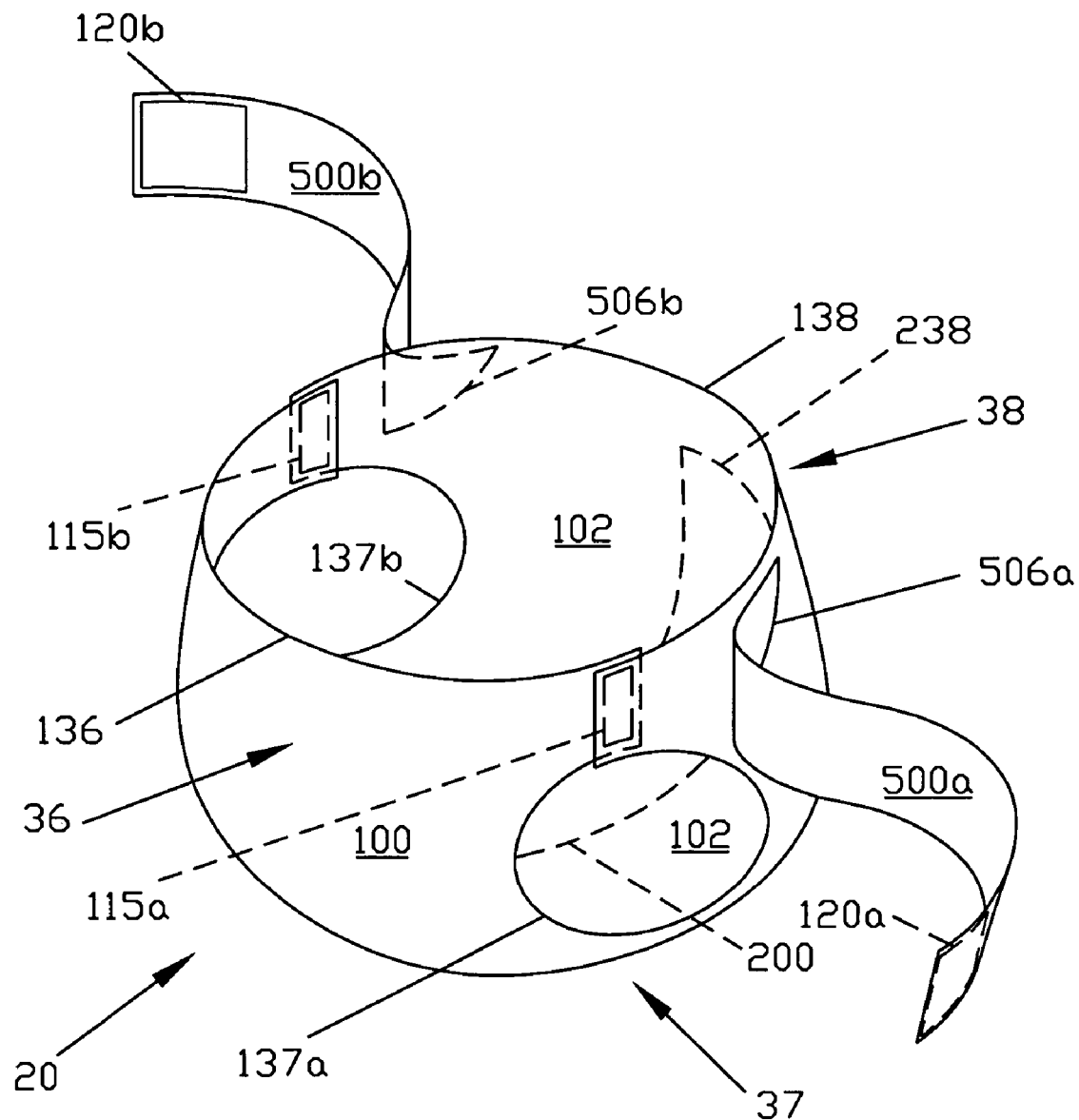
FIG. 36 is a perspective view of an alternative embodiment of a diaper 20.

As shown in FIG. 36, an exemplary diaper 20 having exteriorly disposed belts strips 500 may have side seams 115 at which the front and back waist regions 36 and 38 are non-releasably attached together adjacent to the respective side edges 137 and thereby have the form of pants. In such an embodiment, the belt strips 500 can be used to set and/or adjust the tightness around the waist of the wearer.

Figure 37:
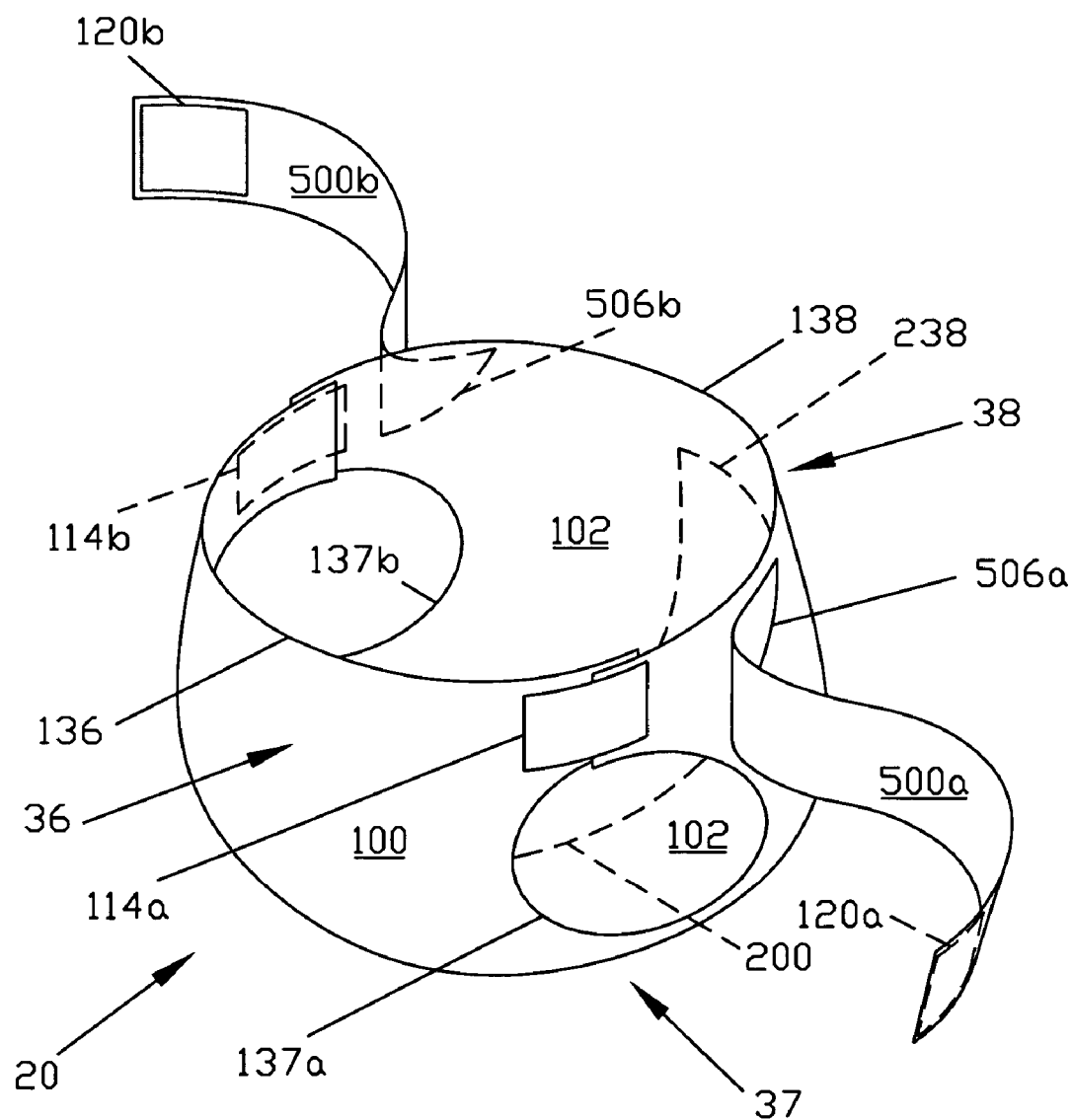
FIG. 37 is a perspective view of another alternative embodiment of a diaper 20.

Similarly, as shown in FIG. 37, an exemplary diaper 20 having exteriorly disposed belts strips 500 may have side fasteners 114 by which the front and back waist regions 36 and 38 are attached together adjacent to the respective side edges 137. The side fasteners 114 may be releasable and refastenable, thereby allowing for easy inspection of the interior of the diaper 20 while it is being worn and subsequent refastening when it is not necessary to change the diaper. The diaper 20 may be provided to the user with the side fasteners 114 already fastened or in an unfastened condition.

The exemplary diaper 20 in FIG. 38 through FIG. 41 has a structure in which an absorbent assembly 200 has a laterally extending front edge 236 in the front waist region 36 and a longitudinally opposing and laterally extending back edge 238 in the back waist region 38. The absorbent assembly 200 also has laterally opposing side edges 237 extending longitudinally between the front edge 236 and the back edge 238. The absorbent assembly 200 includes a lower covering sheet 25 disposed exteriorly of an absorbent core 250.

The absorbent core 250 may be attached to the lower covering sheet 25 over any part or the whole of the area of the absorbent core 250. Preferably, the absorbent core 250 is attached to the lower covering sheet 25 in a cruciform attachment pattern 210, i.e., in an attachment pattern that forms or is arranged in a cross or "+" shape. The portions of the lower covering sheet 25 that lie outside such a cruciform attachment pattern are not restrained by attachment to the absorbent core 250 and therefore remain extensible. In particular, a relatively narrow longitudinally extending portion 212 of a cruciform attachment pattern 210 leaves the majority of the width of the lower covering sheet 25 in the front waist region 36 and in the back waist region 38 freely extensible and thereby allows extension of the lower covering sheet 25 in the lateral direction in these regions. A relatively wide laterally extending portion 214 of a cruciform attachment pattern 210 prevents the portion of the lower covering sheet 25 in the crotch region 37 to which the absorbent core 250 is attached from shifting relative to the absorbent core 250 in that region.

The basic structure of the diaper 20 also includes two laterally opposing longitudinally extending barrier cuff strips 400 in place of the chassis 100 shown in the preceding embodiments. The barrier cuff strips have respective front waist edges 436, back waist edges 438, proximal edges 457, and distal edges 437. The barrier cuff strip distal edges 437 form the respective side edges 137 of the diaper 20. The barrier cuff strips 400 are interiorly attached to the lower covering sheet 25 of the absorbent assembly 200 in laterally opposing longitudinally extending attachment zones 420 and in the front edge and back edge attachment zones 451 located at or adjacent to the front edge 236 and the back edge 238 of the absorbent assembly 200.

The barrier cuff strips 400 are formed of a water vapor-permeable, i.e., breathable, nonwoven material, for example a synthetic nonwoven such as spunbonded or carded polyethylene, polypropylene, polyester, or rayon. The nonwoven material preferably is hydrophobic and the nonwoven barrier cuff strip preferably is water-impermeable. Suitable hydrophobic nonwovens include SM (spunbond meltblown), SMS (spunbond meltblown spunbond), and SMMS (spunbond meltblown meltblown spunbond) composites.

Between the front edge and back edge attachment zones, the proximal edges 457 of the barrier cuff strips 400 remain free, i.e., are not attached to the interior surface 202 of the absorbent assembly 200. Also between the attachment zones, each barrier cuff strip preferably includes a longitudinally extensible cuff elastic member 467 that is attached adjacent to the proximal edge of the barrier cuff strip. Each cuff elastic member 467 may be enclosed inside a hem 471.

Figure 38:
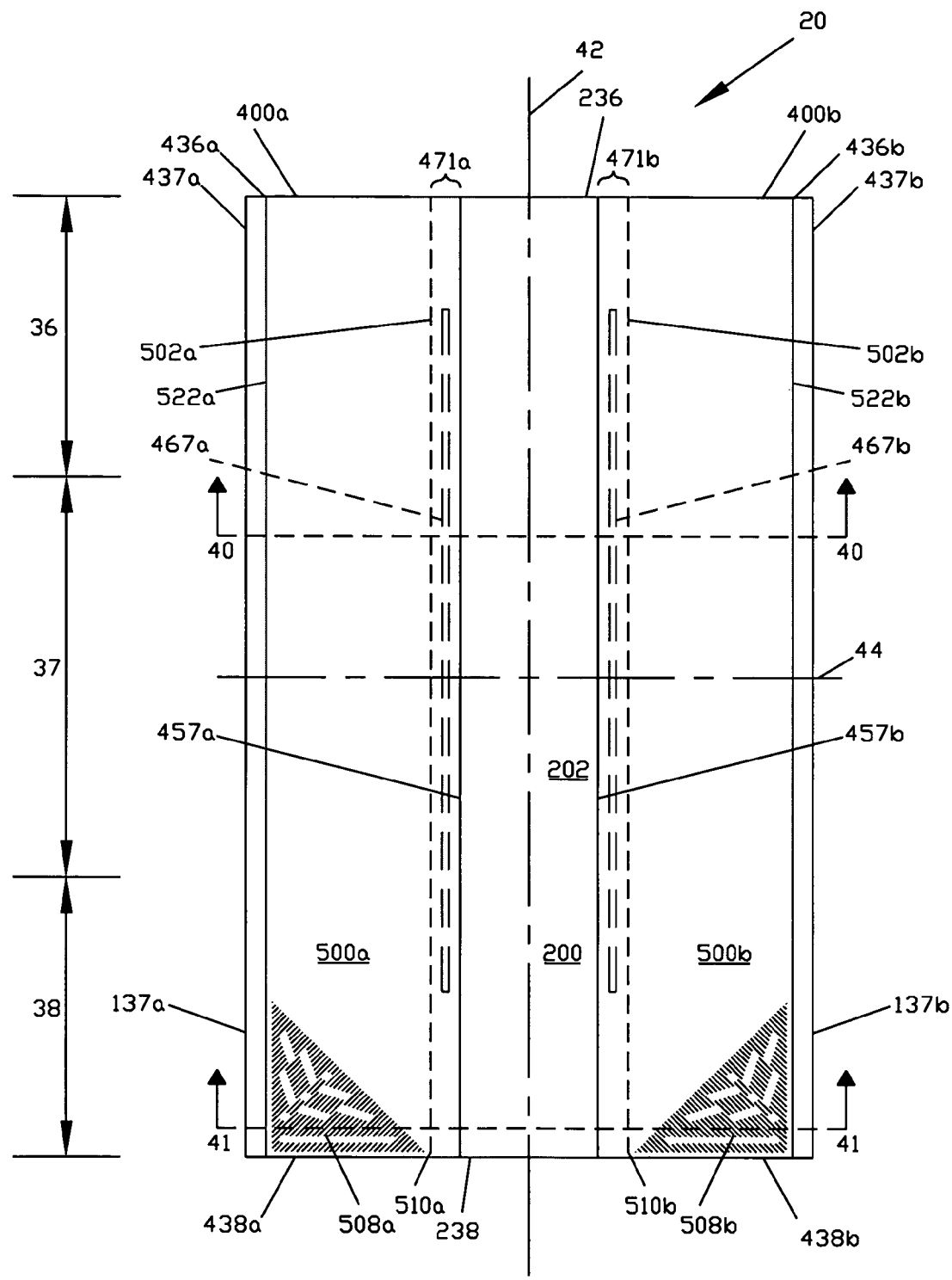
FIG. 38 is an interior plan view of another exemplary disposable diaper 20.
Figure 39:
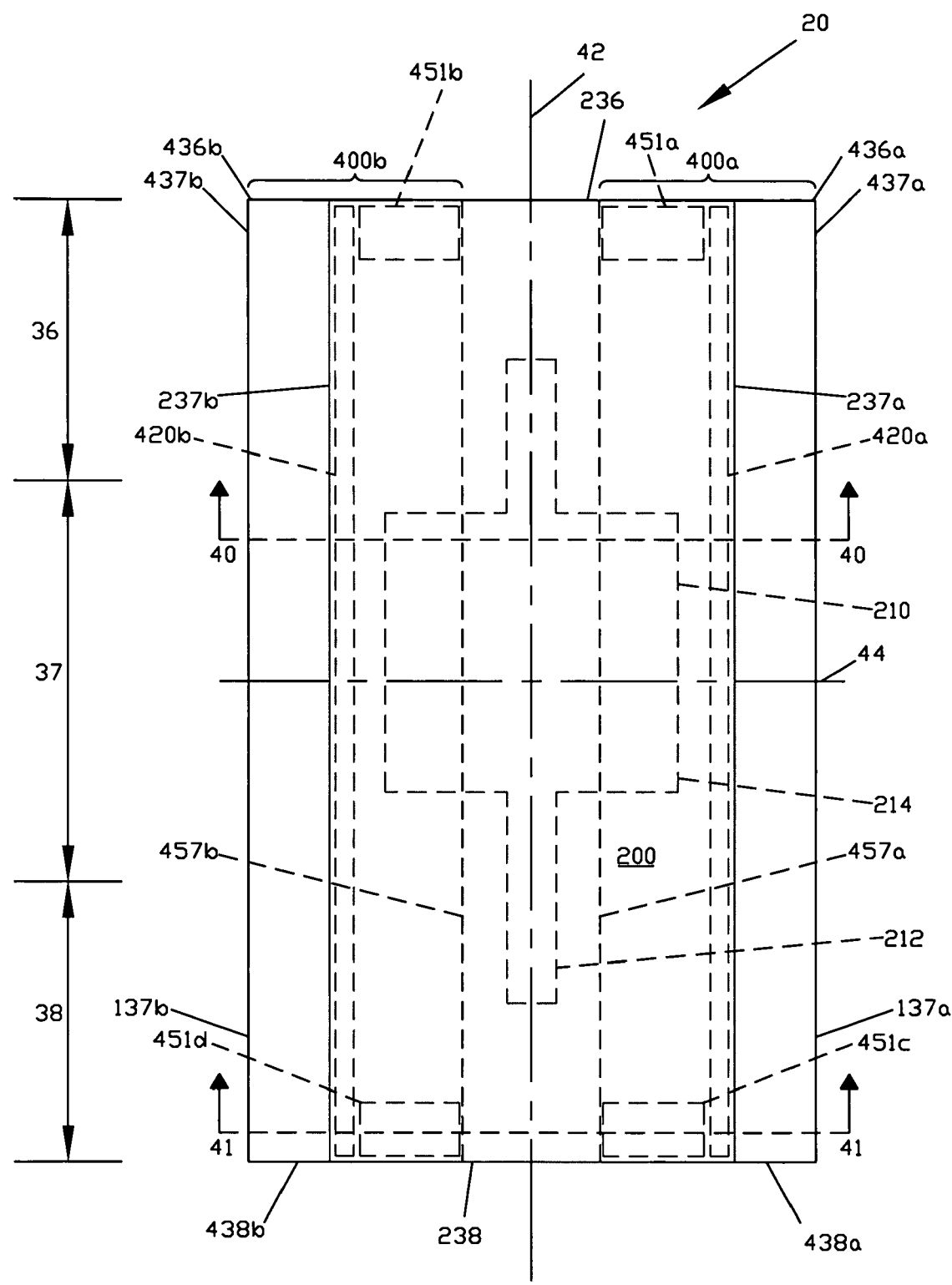
FIG. 39 is an exterior plan view of the disposable diaper 20 of FIG. 38.
Figure 40:
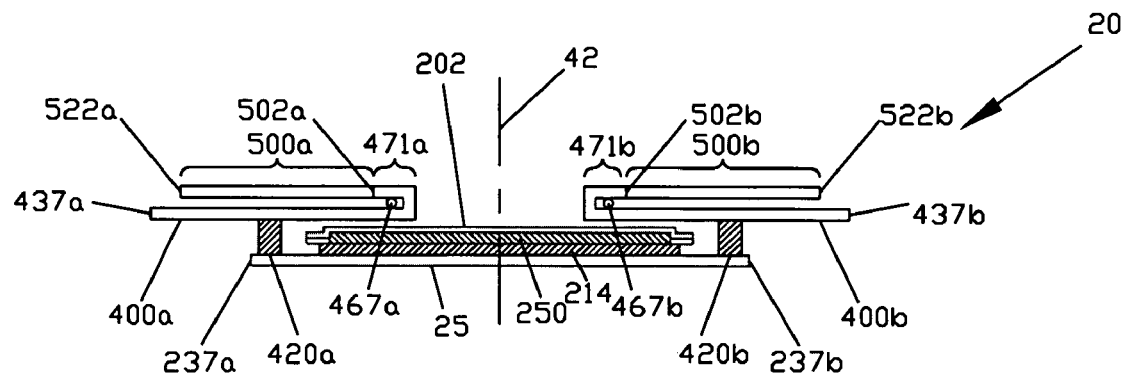
FIG. 40 and FIG. 41 are section views of the diaper 20 of FIG. 38 and FIG. 39 taken at the respective section lines 40-40 and 41-41. In these section views, the interior portion of the diaper 20 is shown facing upward.
Figure 41:
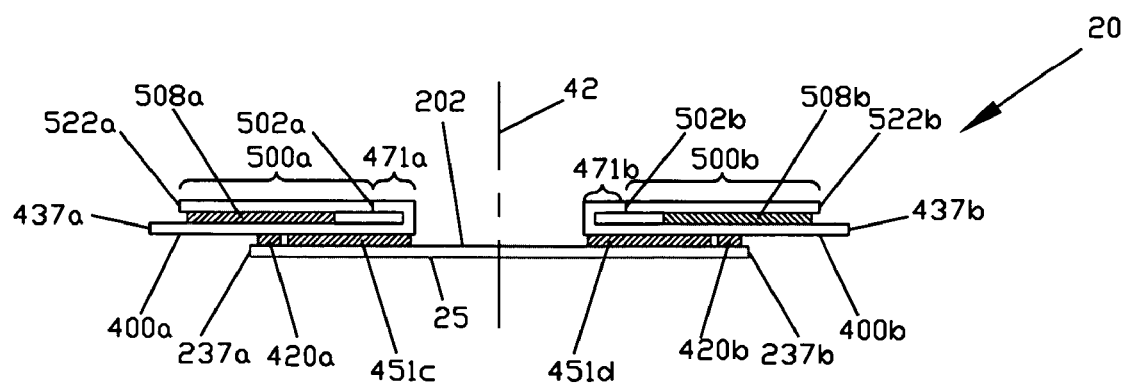

When stretched, the cuff elastic members 467 allow the proximal edges 457 of the barrier cuff strips 400 to extend to the flat uncontracted length of the absorbent assembly 200, as shown in FIG. 38. When allowed to relax, the cuff elastic members contract to gather the portions of the proximal edges 457 along which the cuff elastic members are attached. The contractive forces of the cuff elastic members pull the front waist region 36 and the back waist region 38 toward each other and thereby bend the absorbent assembly 200 and the entire diaper 20 into a "U" shape in which the interior of the "U" shape is formed by the interior portions of the diaper. Because the proximal edges 457 remain free between the attachment zones, the contractive forces of the cuff elastic members lift the proximal edges 457 of the barrier cuff strips 400 away from the interior surface 202 of the absorbent assembly and thereby raise the barrier cuff strips into position to serve as side barriers. The lateral spacing of the lifted proximal edges 457 is selected to allow the deposit of bodily wastes from the lower torso of the wearer into the space between the raised barrier cuff strips. The width of each of the barrier cuff strips 400 preferably is selected to allow the lifted proximal edges 457 to fit into the leg creases of the body of the wearer to form seals to help prevent the leakage of deposited bodily waste out of the diaper.

Several suitable configurations of barrier cuff strips and absorbent assemblies are described in more detail in U.S. Patent Application Publication No. 2005/0288646 of 29 Dec. 2005 and U.S. patent application Ser. No. 11/158,563 filed on 22 Jun. 2005.

A belt strip 500 may be formed contiguously with another structural element of the diaper 20. At least one edge of such a contiguous belt strip 500 is defined by a frangible separation line along which the belt strip 500 can be partially detached for use. Such a frangible separation line may be formed in a layer or a laminate of layers by perforation, by the formation of a brittle area or areas at which the material will preferentially fracture when stressed, by the formation of a weaker area or areas at which the material will preferentially tear when stressed, by the formation of a friable area or areas at which the material will preferentially crumble when stressed and/or bent, or by any other method of providing frangibility that is suitable for the materials involved.

For example, in the diaper 20 shown in FIG. 38 through FIG. 41, each barrier cuff strip 400 is folded laterally outward and each interiorly disposed belt strip 500 is formed from the same layer as the barrier cuff strip 400 by a laterally inboard frangible separation line 502. As can be readily understood by reference to the preceding description of various configurations of belt strips, in this example, each frangible separation line 502 corresponds to the first edge 520 of the respective belt strip 500 and each belt strip 500 can be deployed for use by being partially detached along its frangible separation line 502 and then folded outward along its diagonal fold line (not shown), which is defined during the deployment by its attachment zone 508. In addition to being attached along the frangible separation line 502, if desired for reasons related to handling, packaging, or appearance prior to deployment of the belt strips 500, each belt strip 500 may be releasably attached to another layer with which it is in face-to-face contact. For example, each belt strip 500 may be releasably attached to the barrier cuff strip 400 adjacent to its first edge 520 and/or adjacent to the front edge 236 of the absorbent assembly 200.

Figure 42:
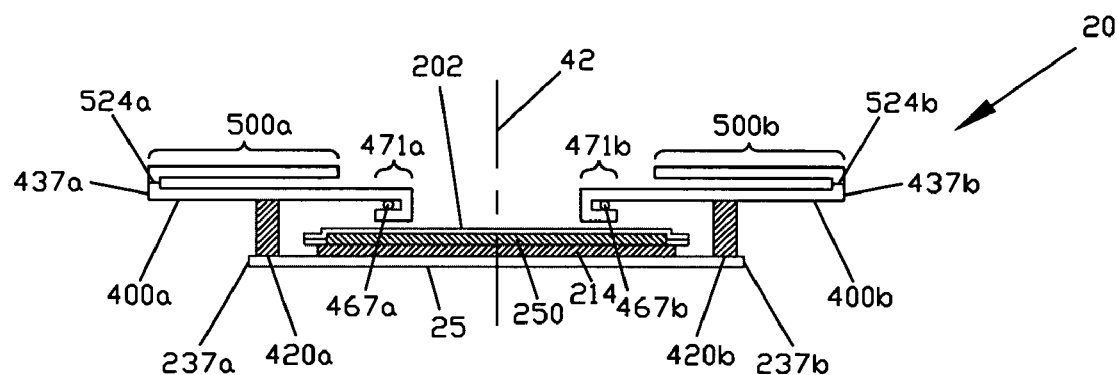
FIG. 42 and FIG. 43 are section views of an alternative embodiment of a diaper 20 taken at section lines corresponding to the respective section lines 40-40 and 41-41. In these section views, the interior portion of the diaper 20 is shown facing upward.
Figure 43:
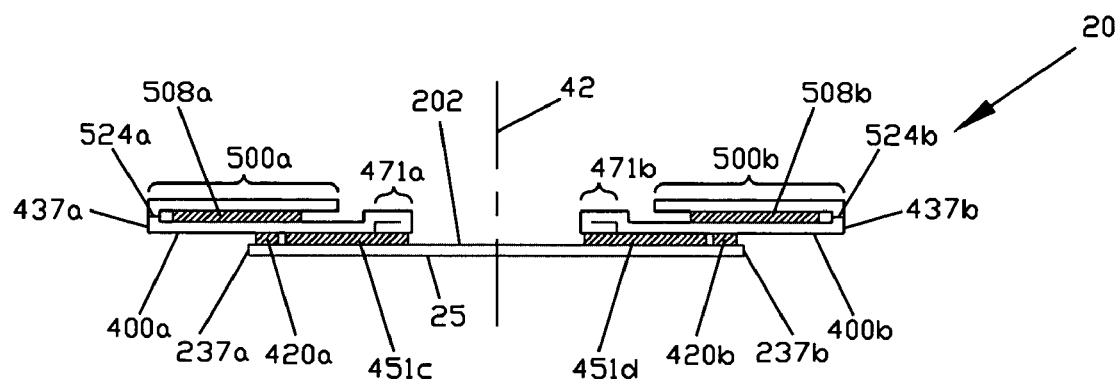

In the next example shown in FIG. 42 and FIG. 43, each barrier cuff strip 400 is folded laterally outward to sandwich its cuff elastic member 467 and is also folded laterally inward at its distal edge 437. In this example, each respective interiorly disposed belt strip 500 is formed from the same layer as the barrier cuff strip 400 by a laterally outboard frangible separation line 524.

Figure 44:
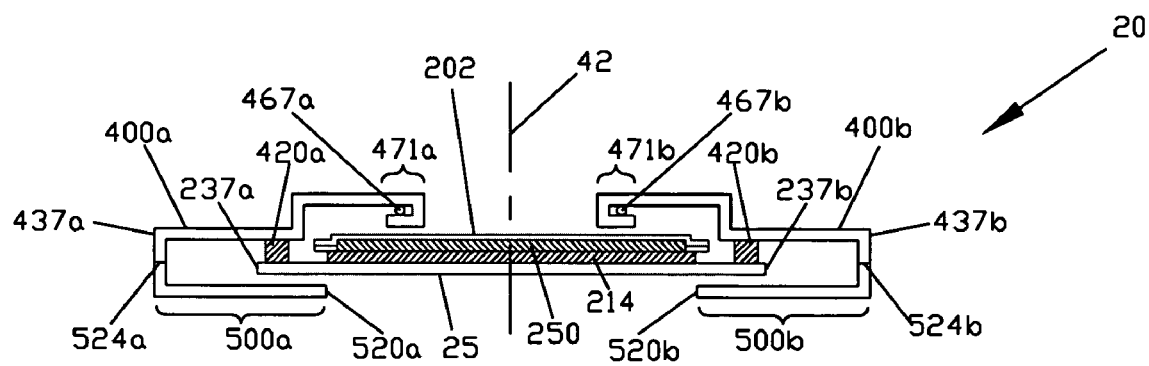
FIG. 44 and FIG. 45 are section views of an alternative embodiment of a diaper 20 taken at section lines corresponding to the respective section lines 40-40 and 41-41. In these section views, the interior portion of the diaper 20 is shown facing upward.
Figure 45:
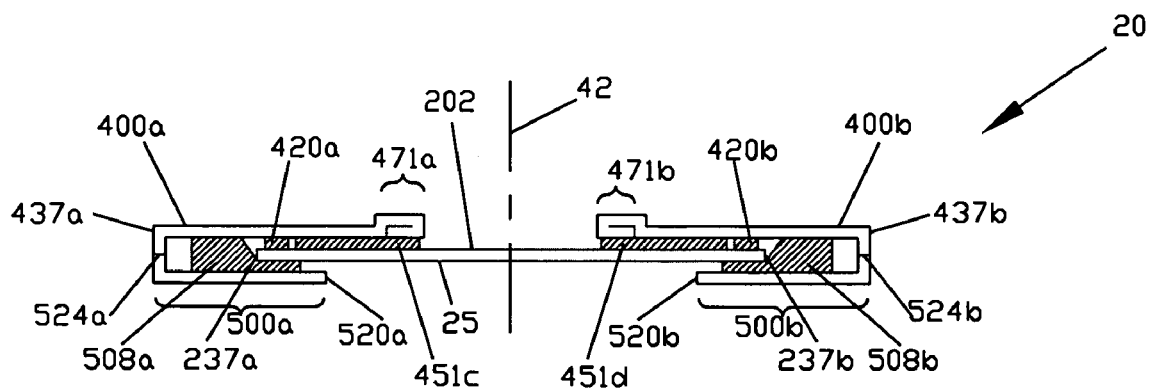

In the exemplary diaper 20 shown in FIG. 44 and FIG. 45, each barrier cuff strip 400 is folded laterally inward to wrap the absorbent assembly 200 at or adjacent to the side edges 237 of the absorbent assembly 200 and the respective exteriorly disposed belt strip 500 is formed from the same layer as the barrier cuff strip 400.

Alternatively, a belt strip 500 may be formed discretely rather than contiguously with another element of the diaper 20. A configuration in which the belt strip is discretely formed may be chosen, for example, when it is desired to use a particular material for the belt strip that is different from either the side flap material or the backsheet material.

Figure 46:
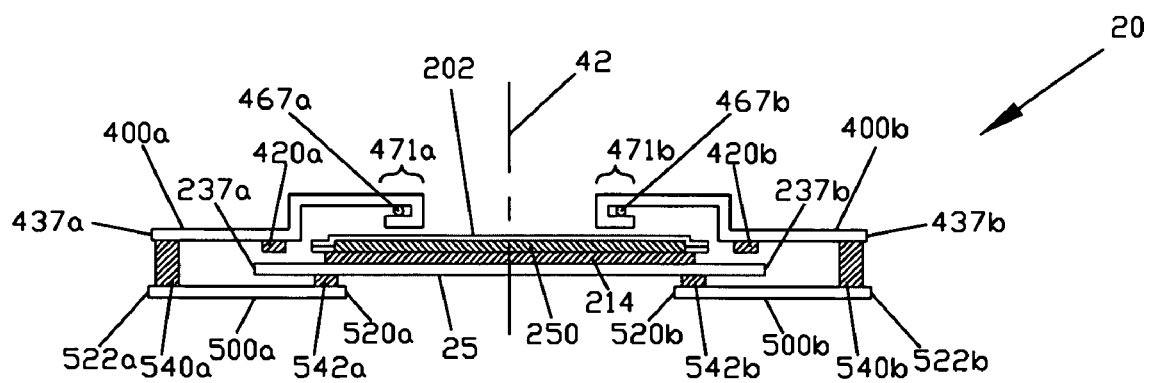
FIG. 46 and FIG. 47 are section views of an alternative embodiment of a diaper 20 taken at section lines corresponding to the respective section lines 40-40 and 41-41. In these section views, the interior portion of the diaper 20 is shown facing upward.
Figure 47:
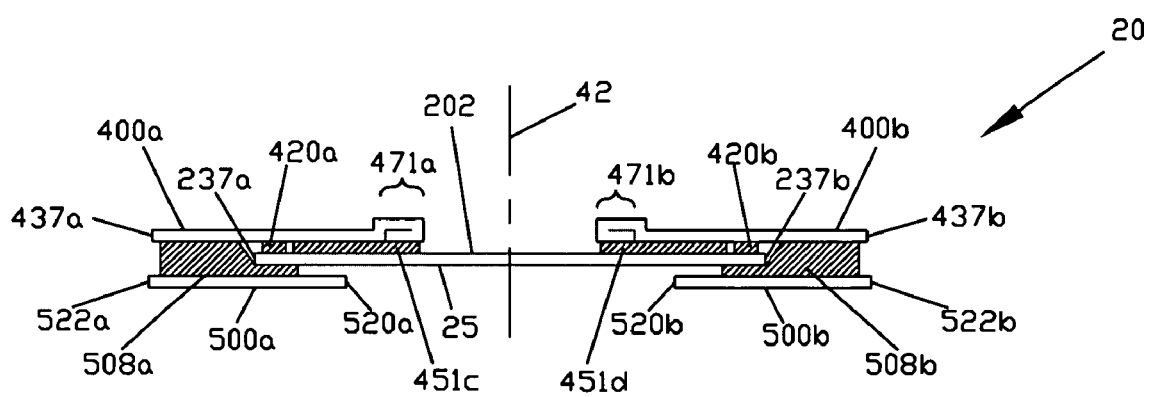
Figure 48:
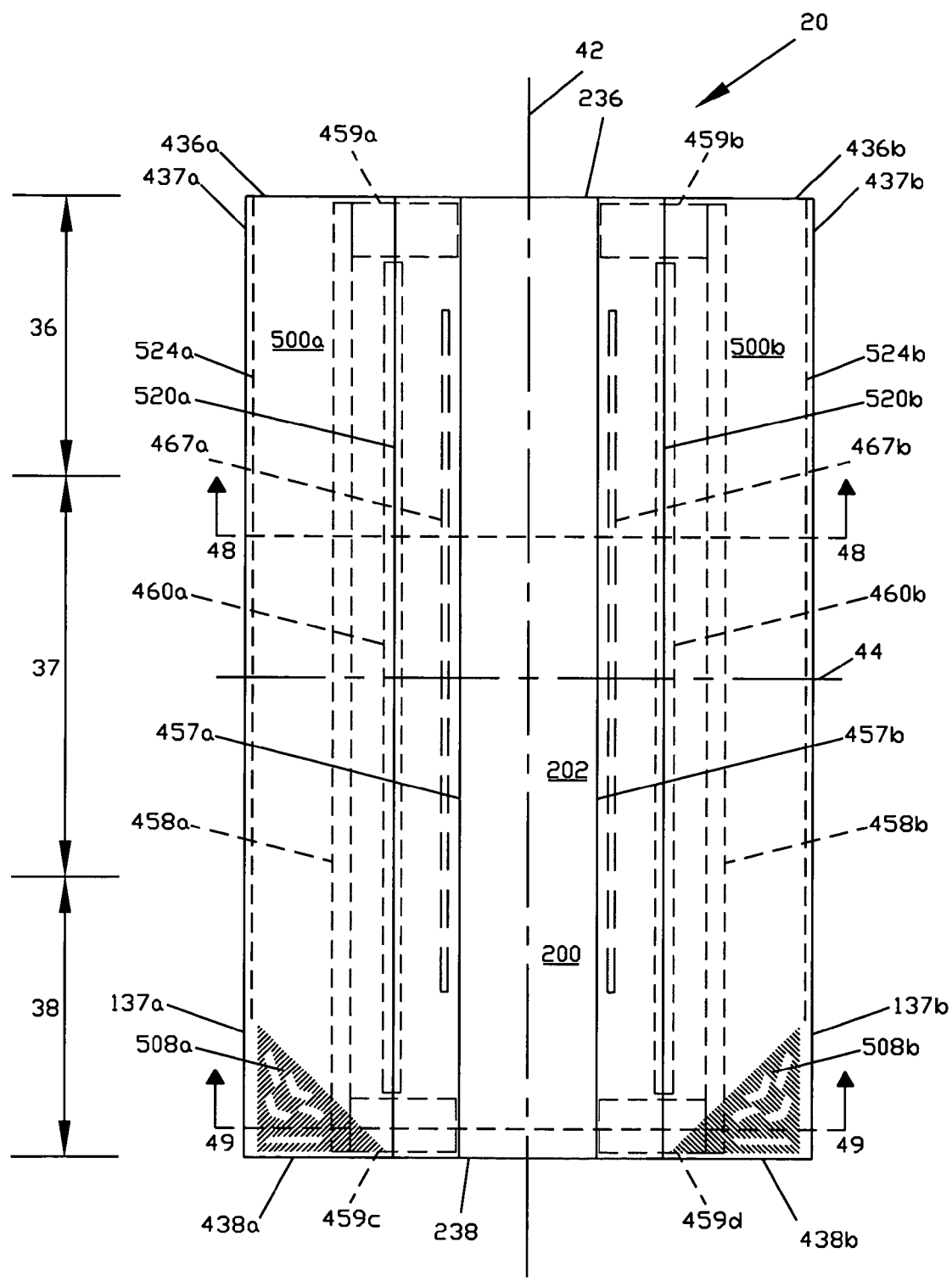
FIG. 48 is an interior plan view of another exemplary disposable diaper 20.
Figure 49:
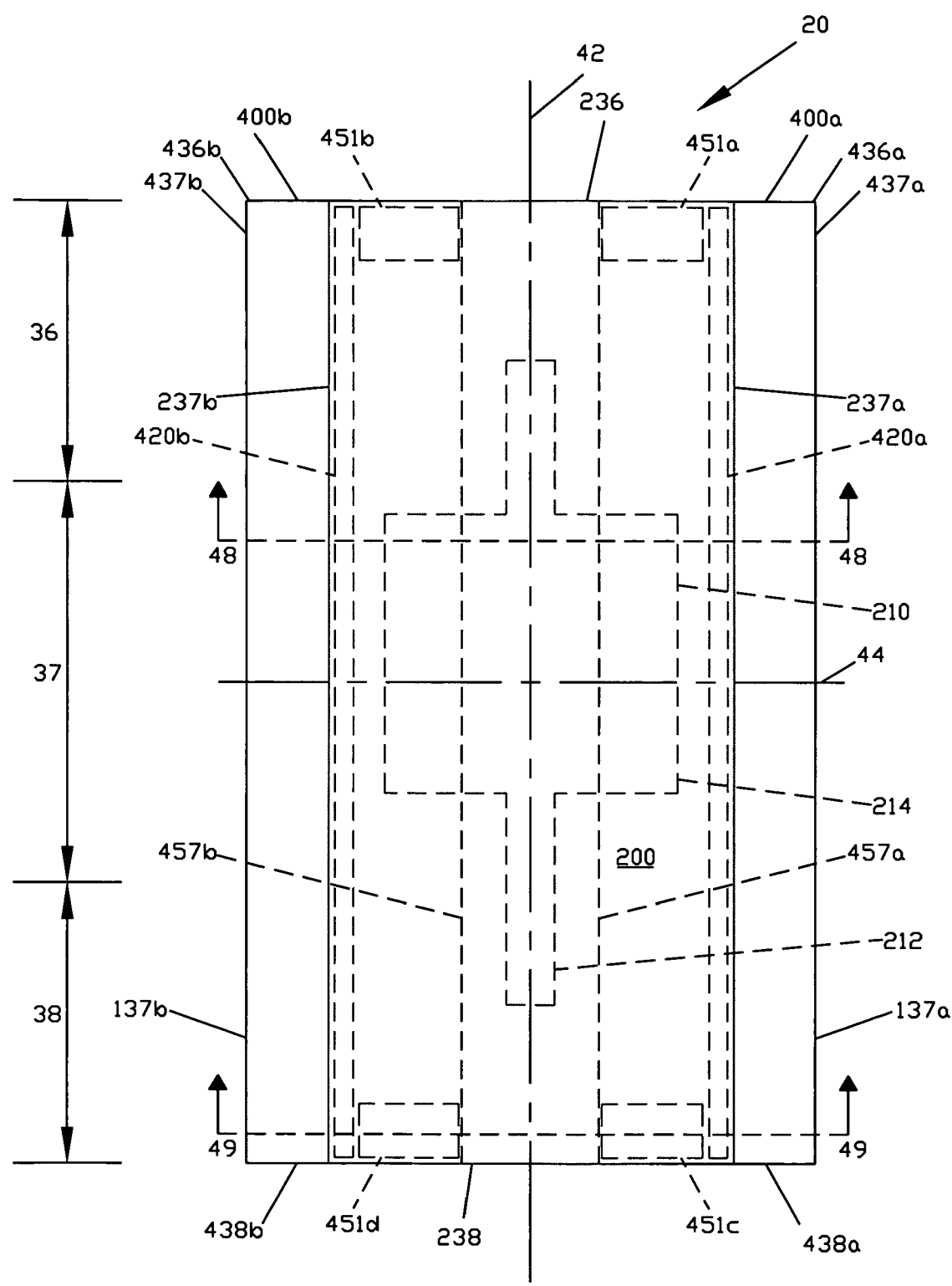
FIG. 49 is an exterior plan view of the disposable diaper 20 of FIG. 48.
Figure 50:
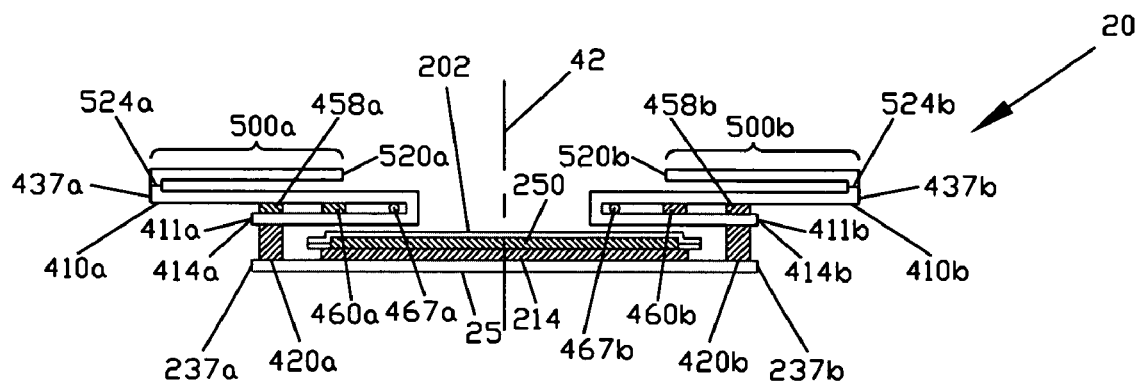
FIG. 50 and FIG. 51 are section views of the diaper 20 of FIG. 48 and FIG. 49 taken at the respective section lines 50-50 and 51-51. In these section views, the interior portion of the diaper 20 is shown facing upward.
Figure 51:
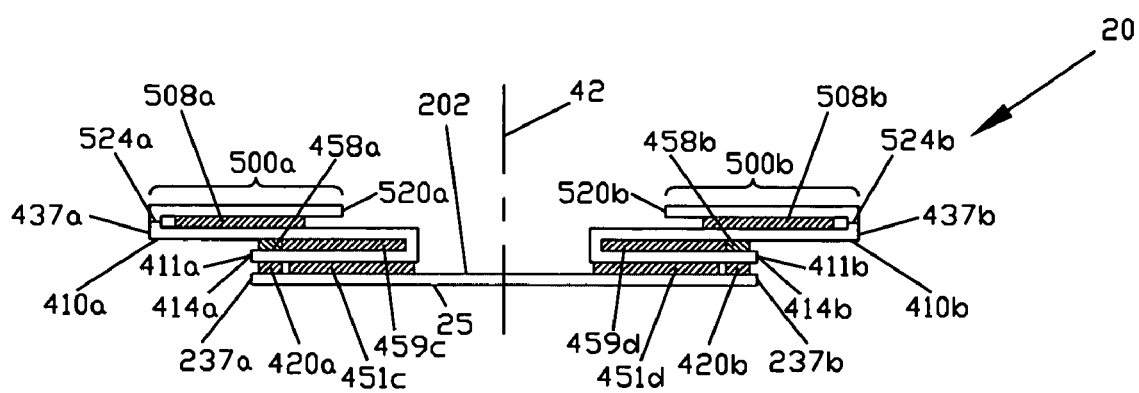

Such discretely formed belt strips may be disposed either interiorly or exteriorly. For example, in the diaper 20 shown in FIG. 46 and FIG. 47, the exteriorly disposed belt strips 500 are releasably attached to the barrier cuff strips 400 and the absorbent assembly 200 at longitudinally extending laterally inboard attachment zones 542 and longitudinally extending laterally outboard attachment zones 540. The belt strips 500 in this example are laterally spaced apart and can be deployed for use by detaching them at the attachment zones 540 and 542 and folding them laterally outward, as in the previous examples. It may be desirable to choose such a configuration in which a belt strip 500 is releasable for deployment at an attachment zone in order to minimize the number of frangible separation lines that must be formed during the manufacture of the diaper 20.

Alternatively, the choice of materials may make the choice of frangible separation lines instead of releasable attachments relatively more desirable. Such frangible separation lines may be located adjacent to the attachment zones 540 and 542 to allow the belt strips 500 to be deployed. Because the frangible separation lines would be present, he attachment zones 540 and 542 would not be releasable as in the preceding example. Such a configuration in which a belt strip 500 is not releasable at its attachment zones may be chosen, for example, when it is desired to avoid the exposure of an adhesive used in the attachment zones 540 and 542 after deployment of the belt strip 500.

In the example shown in FIG. 48 through FIG. 51, each barrier cuff strip 400 is folded laterally inward and each interiorly disposed belt strip 500 is formed from the same layer as the barrier cuff strip 400 by a laterally outboard frangible separation line 524. Each barrier cuff strip 400 in this example includes two layers, namely an upper layer 410 and a lower layer 411, at least between its proximal edge 457 and the attachment zones 420 where the barrier cuff strips 400 and the absorbent assembly 200 are attached together. In this exemplary embodiment, the lower layer 411 of each barrier cuff strip 400 extends less far laterally outward than the upper layer 410 of the same barrier cuff strip. Laterally outward of the attachment zone 420, each barrier cuff strip 400 alternatively may include both of these layers, to equal or unequal lateral extents.

The materials of the water vapor-permeable barrier cuff strips 400 may be selected to balance overall product economics and function. For example, in comparison to the nonwoven materials commonly used in disposable diapers, a relatively inexpensive nonwoven having a relatively low basis weight may provide the requisite level of water-impermeability when it is doubled to form the dual layer barrier cuff strip.

Each barrier cuff strip 400 may be doubled either by folding or by the addition of a second layer. For example, in FIG. 48 through FIG. 51, each barrier cuff strip 400 is folded to form the two layers 410 and 411. As is also shown in these figures, the cuff elastic member 467 may be sandwiched between the folded layers. In this embodiment, the proximal edge 457 of each barrier cuff strip 400 is formed where the barrier cuff strip is folded for doubling.

The lower layer 411 of each doubled barrier cuff strip 400 is attached to the absorbent assembly 200 in the attachment zone 420 adjacent to the respective side edge 237 of the absorbent assembly. The upper layer 410 is in turn attached to the lower layer 411 in an attachment zone 458 disposed either laterally coincidently with the attachment zone 420 or laterally farther outward than the attachment zone 420. For example, the attachment zone 458 is disposed laterally coincidently with the attachment zone 420 in the exemplary diaper shown in FIG. 48 through FIG. 51.

Between the proximal edge 457 and the attachment zone 458, the layers of each doubled barrier cuff strip 400 may remain unattached to each other and thus free to contact each or separate from each other. Alternatively, the layers of each barrier cuff strip 400 may be attached together continuously or intermittently in one or more additional attachment zones located between its proximal edge 457 and the attachment zone 458 and spaced laterally inward from the attachment zone 458. These additional attachment zones extend at least in the crotch region 37 and may extend into one or both of the waist regions 36 and 38. For example, in the exemplary embodiment shown in FIG. 48 through FIG. 51, the layers are attached together in laterally spaced additional attachment zones 460 extending longitudinally through the crotch region 37 and into the waist regions 36 and 38. Such additional attachment together prevents the layers from separating and thereby presenting an undesirable baggy or blousy appearance around the legs of the wearer, as well as tending to stiffen the doubled barrier cuff strips 400 slightly and thereby helping to ensure their proper fit against the body. The layers of each doubled barrier cuff strip may be attached together by adhesives, mechanical bonds, or thermal bonds, or by a combination of known bonding methods.

Alternatively, or in addition, the layers of the each doubled barrier cuff strip 400 may be attached together in the waist regions 36 and 38 adjacent to the waist edges 436 and 438, for example in laterally extending attachment zones 459. This lateral attachment may be laterally intermittent or laterally continuous. When such a laterally extending attachment zone is laterally continuous from the proximal edge 457 to the attachment zone 458 where the upper layer 410 is attached to the lower layer 411, as in FIG. 48 and FIG. 51, it prevents the layers from separating and thereby presenting an undesirable unfinished appearance at the waist edges, as well as preventing the leakage at the waist edge of any liquid waste from between the layers.

Figure 52:
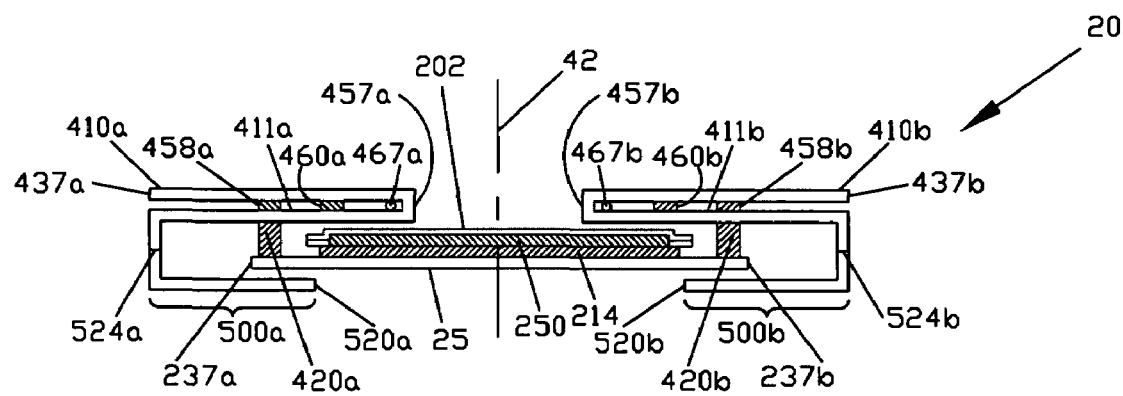
FIG. 52 and FIG. 53 are section views of an alternative embodiment of a diaper 20 taken at section lines corresponding to the respective section lines 50-50 and 51-51. In these section views, the interior portion of the diaper 20 is shown facing upward.
Figure 53:
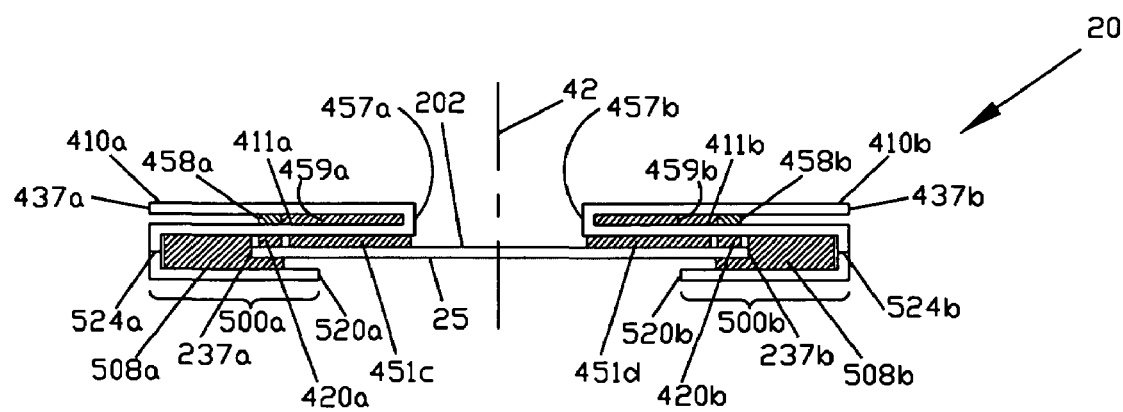

In the next example shown in FIG. 52 and FIG. 53, each barrier cuff strip 400 is again doubled by folding and each belt strip 500 is again formed from the same layer as the barrier cuff strip 400 by a laterally outboard frangible separation line 524. However, in this example, in FIG. 44 and FIG. 45, each doubled barrier cuff strip 400 is folded laterally inward to wrap the absorbent assembly 200 at or adjacent to the side edges 237 of the absorbent assembly 200 and the respective belt strip 500 is thus exteriorly disposed.

Figure 54:
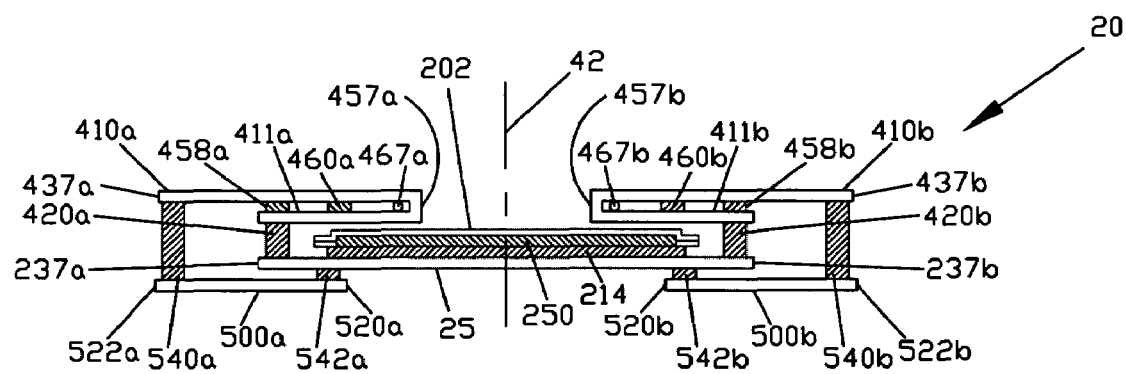
FIG. 54 and FIG. 55 are section views of an alternative embodiment of a diaper 20 taken at section lines corresponding to the respective section lines 50-50 and 51-51. In these section views, the interior portion of the diaper 20 is shown facing upward.
Figure 55:
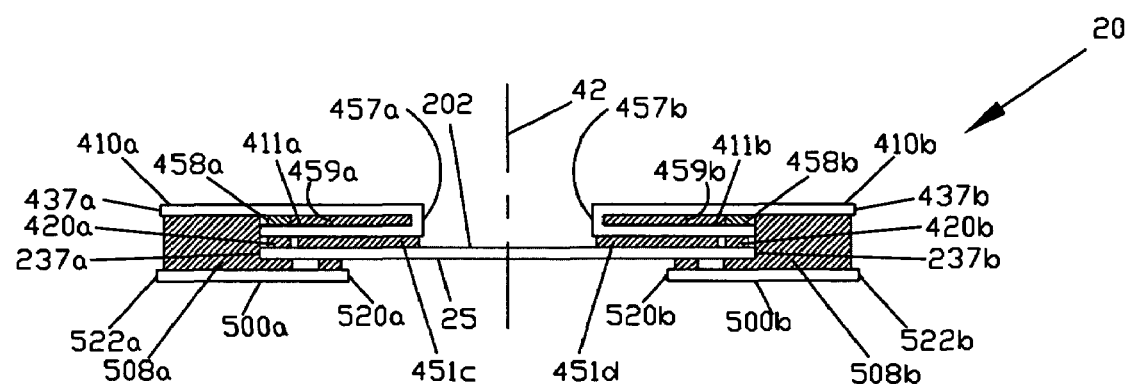

In the exemplary diaper 20 shown in FIG. 54 and FIG. 55, the discretely formed exteriorly disposed belt strips 500 are releasably attached to the doubled barrier cuff strips 400 and the absorbent assembly 200 at longitudinally extending laterally inboard attachment zones 542 and longitudinally extending laterally outboard attachment zones 540. The belt strips 500 in this example are laterally spaced apart and can be deployed for use by detaching them at the attachment zones 540 and 542 and folding them laterally outward, as in the previous examples. Alternatively, frangible separation lines may be located adjacent to the attachment zones 540 and 542 to allow the belt strips 500 to be deployed, as in a preceding example.

The preceding examples are provided in order to convey to those of skill in the art that the deployable belt strips of the present invention can be provided in a variety of configurations. The above examples are not exhaustive, i.e., variations in addition to these are foreseen. For example, each of the mentioned layers may be formed of two or more members and thus may be laminates and/or composites of such members. As another example, each of the mentioned layers may be doubled by folding such that, for example, a belt strip 500 may be doubled and have one edge defined by a fold. The intent is to convey the concept of the present invention, i.e., a diaper incorporating deployable belt strips, while avoiding unnecessary length and complexity in this description. This voluntary characterization of the present invention is expressly not intended to constitute a surrender of any potential scope of any patentable claim(s).

The disclosures of all patents, patent applications and any patents which issue thereon, as well as any corresponding published foreign patent applications, and all publications listed and/or referenced in this description, are hereby incorporated in their entireties herein by reference. It is expressly not admitted that any of the documents or any combination of the documents incorporated herein by reference teaches or discloses the present invention.

What is claimed is:

1. A disposable diaper having longitudinally opposing front and back waist regions having waist edges, laterally opposing side edges connecting the waist edges, a crotch region between the waist regions, and comprising:
   an absorbent assembly having an interior surface;
   two laterally opposing longitudinally extending barrier cuff strips attached to the interior surface, each barrier cuff strip having a longitudinally extending cuff elastic member attached adjacent to its proximal edge; and
   at least one belt strip having a fixed end portion, an opposing free end portion, a first edge, and a second edge, the first edge and the second edge connecting the end portions, the belt strip being attached in the fixed end portion to one of the waist regions and additionally being attached along at least a portion of one of the first edge and the second edge,
   the belt strip being deployed by being detached except at its fixed end portion and folded laterally outward at a diagonal fold line having opposing end points such that the first edge extends laterally outward from one end point and the second edge extends laterally outward from the opposing end point.

2. The disposable diaper of claim 1 wherein, prior to its deployment, the belt strip extends to the waist edge of the waist region opposing its fixed end portion.

3. The disposable diaper of claim 1 wherein, prior to its deployment, the belt strip extends only from the waist region in which its fixed end portion is disposed into the crotch region.

4. The disposable diaper of claim 1 having only a single belt strip extending when deployed from the waist region where its fixed end portion is disposed to and laterally across the opposing waist region and further to the waist region where its fixed end portion is disposed and thereby connecting the waist regions at both of the side edges.

5. The disposable diaper of claim 1 having two laterally opposing belt strips.

6. The disposable diaper of claim 5 wherein the belt strips are laterally spaced apart.

7. The disposable diaper of claim 5 wherein the belt strips are laterally abutted.

8. The disposable diaper of claim 5 wherein, after their deployment, the belt strips are tied together exteriorly of the waist region opposing their fixed end portions.

9. The disposable diaper of claim 5 wherein, after their deployment, the belt strips are attached by a fastener to the waist region opposing their fixed end portions.

10. The disposable diaper of claim 1 having two laterally opposing belt strips having their fixed end portions disposed in the front waist region and two laterally opposing belt strips having their fixed end portions disposed in the back waist region.

11. The disposable diaper of claim 10 wherein, after their deployment, two of the belt strips are tied together adjacent to one of the side edges and the other two of the belt strips are tied together adjacent to the opposing side edge.

12. The disposable diaper of claim 10 wherein, after their deployment, two of the belt strips are attached together by a fastener adjacent to one of the side edges and the other two of the belt strips are attached together by another fastener adjacent to the opposing side edge.

13. The disposable diaper of claim 1 wherein the belt strip is formed contiguously with another structural element of the disposable diaper.

14. The disposable diaper of claim 13 wherein the belt strip is detachable from the other structural element along a frangible separation line.

15. The disposable diaper of claim 1 wherein the belt strip is formed from a discrete strip attached to the absorbent assembly.

16. The disposable diaper of claim 1 wherein the fixed end portion is attached in an attachment zone extending longitudinally and laterally outward from the diagonal fold line.

17. A disposable diaper having longitudinally opposing front and back waist regions having waist edges, laterally opposing side edges connecting the waist edges, a crotch region between the waist regions, and comprising:
   an absorbent assembly having an interior surface;

two laterally opposing longitudinally extending barrier cuff strips attached to the interior surface, each barrier cuff strip having a longitudinally extending cuff elastic member attached adjacent to its proximal edge; and at least one exteriorly disposed belt strip having a fixed end portion disposed in one of the waist regions, an opposing free end portion, a first edge and a second edge, the first edge and the second edge connecting the end portions, the belt strip being folded laterally outward at a diagonal fold line such that the first edge extends laterally outward from a laterally proximal end point of the diagonal fold line and the second edge extends laterally outward from a laterally distal end point of the diagonal fold line.

18. The disposable diaper of claim 17 wherein the belt strip is formed contiguously with another structural element of the disposable diaper.

19. The disposable diaper of claim 17 wherein the belt strip is formed from a discrete strip attached to the absorbent assembly.

20. A disposable diaper having longitudinally opposing front and back waist regions having waist edges, laterally opposing side edges connecting the waist edges, a crotch region between the waist regions, and comprising:

an absorbent assembly having an interior surface;

two laterally opposing longitudinally extending barrier cuff strips attached to the interior surface, each barrier cuff strip having a longitudinally extending cuff elastic member attached adjacent to its proximal edge; and at least one interiorly disposed belt strip having a fixed end portion disposed in one of the waist regions, an opposing free end portion, a first edge and a second edge, the first edge and the second edge connecting the end portions, the belt strip being folded laterally outward at a diagonal fold line such that the first edge extends laterally outward from a laterally proximal end point of the diagonal fold line and the second edge extends laterally outward from a laterally distal end point of the diagonal fold line.

* * * * *